(12) United States Patent
Sasagawa et al.

(10) Patent No.: US 11,980,791 B2
(45) Date of Patent: May 14, 2024

(54) LIVING BODY GUIDANCE APPARATUS, LIVING BODY GUIDANCE METHOD AND LIVING BODY GUIDANCE PROGRAM

(71) Applicant: NIPPON TELEGRAPH AND TELEPHONE CORPORATION, Tokyo (JP)

(72) Inventors: Mana Sasagawa, Musashino (JP); Arinobu Niijima, Musashino (JP); Kana Eguchi, Musashino (JP); Ryosuke Aoki, Musashino (JP); Takashi Isezaki, Musashino (JP); Tomoki Watanabe, Musashino (JP); Toshitaka Kimura, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 297 days.

(21) Appl. No.: 17/596,370

(22) PCT Filed: Jun. 12, 2019

(86) PCT No.: PCT/JP2019/023373
§ 371 (c)(1),
(2) Date: Dec. 8, 2021

(87) PCT Pub. No.: WO2020/250361
PCT Pub. Date: Dec. 17, 2020

(65) Prior Publication Data
US 2022/0233916 A1  Jul. 28, 2022

(51) Int. Cl.
*A63B 24/00* (2006.01)
*A61B 5/296* (2021.01)
*A61B 5/395* (2021.01)

(52) U.S. Cl.
CPC .......... *A63B 24/0006* (2013.01); *A61B 5/296* (2021.01); *A61B 5/395* (2021.01); *A63B 2024/0012* (2013.01)

(58) Field of Classification Search
None
See application file for complete search history.

(56) References Cited

U.S. PATENT DOCUMENTS 9,047,746 B1 * 6/2015 Euliano, II ............... A61B 5/07
9,524,424 B2 * 12/2016 Greene .................. A61B 5/112
(Continued)

FOREIGN PATENT DOCUMENTS

JP   H0736362 A   2/1995
JP   2017522 A    1/2017

OTHER PUBLICATIONS

Inflasole, "Adjustable Comfort Insoles—Just Pump-It-Up! Inflatable Replaceable Inserts for Shoes, Foot Leveler". May 21, 2019 (Reading Day). http://www.inflasole.com/pages/instructions.html.
(Continued)

*Primary Examiner* — Fekadeselassie Girma
(74) *Attorney, Agent, or Firm* — Harness, Dickey & Pierce, P.L.C.

(57) ABSTRACT

A living body guidance device includes: a measurement unit 1 that measures biometric information of a user; a stimulus unit 2 that is installed in contact with the user's body and presents a tactile stimulus to the user; a database unit 3 that has a relationship between the tactile stimulus presented by the stimulus unit and the biometric information according to the tactile stimulus recorded; an input unit 4 that sets target biometric information which is target biometric information that is desired of the user to realize; and a control unit 7 that, when there is a difference between current biometric information which is current biometric information of the user estimated based on the measurement result by the measure-
(Continued)

ment unit and the target biometric information, controls the tactile stimulus presented by the stimulus unit so that the difference is reduced, so as to guide the user so that the current biometric information approaches the target biometric information, based on the relationship recorded in the database unit, by.

13 Claims, 13 Drawing Sheets

(56) References Cited

U.S. PATENT DOCUMENTS

| | | | | |
|---|---|---|---|---|
| 9,836,118 | B2* | 12/2017 | Steele | G06F 3/011 |
| 9,877,667 | B2* | 1/2018 | Doheny | G16Z 99/00 |
| 10,152,898 | B2* | 12/2018 | Rhea | G09B 5/02 |
| 10,307,084 | B2* | 6/2019 | Forth | A61B 5/7275 |
| 10,405,780 | B2* | 9/2019 | Finch | A61B 5/1124 |
| 10,521,561 | B1* | 12/2019 | Euliano | A61B 5/4839 |
| 10,524,698 | B2* | 1/2020 | Annegarn | G08B 31/00 |
| 10,535,015 | B2* | 1/2020 | Ahn | G06N 20/00 |
| 11,277,697 | B2* | 3/2022 | Burwinkel | G08B 21/0453 |
| 2008/0231458 | A1* | 9/2008 | Fein | H01Q 1/2225 |
| | | | | 340/572.7 |
| 2011/0046519 | A1* | 2/2011 | Raheman | A61B 5/1123 |
| | | | | 600/595 |
| 2012/0119904 | A1* | 5/2012 | Coleman Boone | G01C 22/006 |
| | | | | 702/160 |
| 2014/0309505 | A1* | 10/2014 | Euliano | A61B 5/073 |
| | | | | 600/302 |
| 2018/0055415 | A1* | 3/2018 | Nakao | A61B 5/224 |
| 2018/0085653 | A1* | 3/2018 | Picker | G09B 5/02 |
| 2019/0261920 | A1* | 8/2019 | Euliano | A61B 5/4205 |
| 2022/0001236 | A1* | 1/2022 | Mooney | G06F 18/00 |

OTHER PUBLICATIONS

Katerina Baousi et al. "Inflashoe: A Shape Changing Shoe to Control Underfoot Pressure". In Proceedings of the 2017 CHI Conference Extended Abstracts on Human Factors in Computing Systems (CHI EA'17). May 6, 2017.

Mahmoud Hassan et al. "FootStriker: An EMS-based Foot Strike Assistant for Running". Proceedings of the ACM on Interactive. vol. 1, No. 1, 2017.

* cited by examiner

Fig. 4

| HARDNESS | iEMG ($\mu$V) |
|---|---|
| HARD | 30 |
| SOFT | 70 |

Fig. 5

| HARDNESS | DRIVE AMOUNT (Pa) |
|---|---|
| HARD | XX |
| SOFT | YY |

| OPERATION PERIOD | Px | Py |
|---|---|---|
| iEMG (μV) | 10 | 60 |
| | ⋮ | ⋮ | ously
LIVING BODY GUIDANCE APPARATUS, LIVING BODY GUIDANCE METHOD AND LIVING BODY GUIDANCE PROGRAM

CROSS-REFERENCE TO RELATED APPLICATIONS

This application is a 371 U.S. National Phase of International Application No. PCT/JP2019/023373 filed on Jun. 12, 2019. The entire disclosures of the above applications are incorporated herein by reference.

TECHNICAL FIELD

The present invention relates to a living body guidance device, a living body guidance method and a living body guidance program.

BACKGROUND ART

In sports and rehabilitation, a coach or trainer with know-how has conventionally provided guidance to help a user change a movement to an appropriate movement (for example, how to kick a ball farther, how to move one's foot like a healthy person, etc.).

In addition, a method of providing assistance using a correction appliance has also been proposed.

For example, NPL 1 and 2 disclose insoles of which properties can be changed by the user so as to be suited to the user.

NPL 3 proposes a method of applying an electrical stimulus in order to change a movement of a user to an appropriate movement.

In addition, there is a method of using a power assist suit that adds power to amplify a movement of a user.

CITATION LIST

Non Patent Literature

[NPL 1] "ADJUSTABLE COMFORT INSOLES—Just Pump-It-Up! Inflatable Replaceable Inserts for Shoes, Foot Leveler."[Online], [retrieved on May 21, 2019], Internet <URL: http://www.inflasole.com/pages/instructions.html>

[NPL 2] Katerina Baousi, Nate Fear, Christos Mourouzis, Ben Stokes, Henry Wood, Paul Worgan, and Anne Roudaut. 2017. Inflashoe: A Shape Changing Shoe to Control Underfoot Pressure. In Proceedings of the 2017 CHI Conference Extended Abstracts on Human Factors in Computing Systems (CHI EA'17). ACM, New York, NY, USA, 2381-2387.

[NPL 3] Mahmoud Hassan, Florian Daiber, Frederik Wiehr, Felix Kosmalla, and Antonio Kruger. 2017. FootStriker: An EMS-based Foot Strike Assistant for Running. Proc. ACM Interact. Mob. Wearable Ubiquitous Technol. 1, 1, Article 2 (March 2017), 18 pages.

SUMMARY OF THE INVENTION

Technical Problem

When the user tries to change the movement to an appropriate movement based only on an instruction from the coach or trainer, the user himself or herself has not experienced the appropriate movement, that is, the target movement. Therefore, the user does not know how to change his or her own movement to approach the target movement, and may end up not achieving the target movement.

When a correction appliance is used, in the correction appliances disclosed in NPL 1 and 2, when the situation of the user himself or herself or the surrounding environment changes, the correction appliance should be removed once and adjusted. Therefore, not only is it time-consuming but it is also not possible to handle when the user performs an operation.

In the method disclosed in NPL 3 in which an electrical stimulus is applied so that the movement is forcibly changed to a target movement that the user wants to realize, the user does not have an ability to control muscle movement. Therefore, when erroneous control is performed, there is a risk of a movement outside a movable range of the user occurring, which may be dangerous to the user.

In the method using a power assist suit, since power is added, it is possible to perform a movement equal to or greater than the muscle strength of the user. Therefore, when the device is removed, if the muscle strength of the user is insufficient, it is not always possible to achieve the target movement to be realized. In addition, since the power assist suit amplifies a current movement of the user, it is not possible to make the user move with a power vector different from that of the current movement.

The present invention has been made in view of the above circumstances, and an object of the present invention is to provide a living body guidance device, a living body guidance method and a living body guidance program through which it is possible to apply an appropriate and safe tactile stimulus for guiding the user to perform a target movement to be realized.

Means for Solving the Problem

According to a first aspect of the present invention, provided is a living body guidance device including: a measurement unit that measures biometric information of a user; a stimulus unit that is installed in contact with the user's body and presents a tactile stimulus to the user; a database unit that has a relationship between the tactile stimulus presented by the stimulus unit and the biometric information according to the tactile stimulus of the stimulus unit recorded; an input unit that sets target biometric information which is target biometric information to be realized; and a control unit that, when there is a difference between current biometric information which is current biometric information of the user estimated based on the measurement result of the measurement unit and the target biometric information set by the input unit, controls the tactile stimulus presented by the stimulus unit, based on the relationship recorded in the database unit, so that the difference is reduced, so as to guide the user so that the current biometric information approaches the target biometric information.

According to a second aspect of the present invention, provided is a living body guidance method, wherein a computer is caused to: measure biometric information of a user; receive target biometric information which is target biometric information that is desired of the user to realize; when there is a difference between current biometric information which is current biometric information of the user estimated based on the measurement result of the biometric information of the user and the target biometric information, controls a tactile stimulus presented by a stimulus unit so that the difference is reduced, so as to guide the user so that the current biometric information approaches the target biometric information, based on a relationship recorded in a database unit in which the relationship between the tactile stimulus presented to the user by the stimulus unit installed in contact with the user's body and the biometric information according to the tactile stimulus of the stimulus unit is recorded; and repeat at least measurement of the biometric information and guiding of the user until the difference between the target biometric information and the current biometric information disappears or until the current biometric information stops changing.

According to a third aspect of the present invention, provided is a living body guidance program for causing a processor of a living body guidance device including the processor and a storage to function as: a measurement unit that measures biometric information of a user; an input unit that sets target biometric information which is target biometric information desired of the user to realize; and a control unit that, when there is a difference between current biometric information which is current biometric information of the user estimated based on the measurement result of biometric information of the user and the target biometric information, controls a tactile stimulus presented by a stimulus unit so that the difference is reduced by referring to a database unit provided in the storage that has a relationship between the tactile stimulus presented to the user by the stimulus unit installed in contact with the user's body and the biometric information according to the tactile stimulus of the stimulus unit recorded, so as to guide the user so that the current biometric information approaches the target biometric information, based on the relationship recorded in the database unit.

Effects of the Invention

According to the present invention, it is possible to provide a living body guidance device, a living body guidance method and a living body guidance program through which it is possible to apply an appropriate and safe tactile stimulus for guiding the user to perform a target movement that the user wants to realize.

BRIEF DESCRIPTION OF DRAWINGS

FIG. 4 is a diagram showing a content example of a database unit provided in a storage of a user terminal.

FIG. 5 is a diagram showing a content example of the database unit provided in the storage of the user terminal.

DESCRIPTION OF EMBODIMENTS

Hereinafter, embodiments of the invention will be described with reference to the drawings.

First Embodiment

Figure 1:
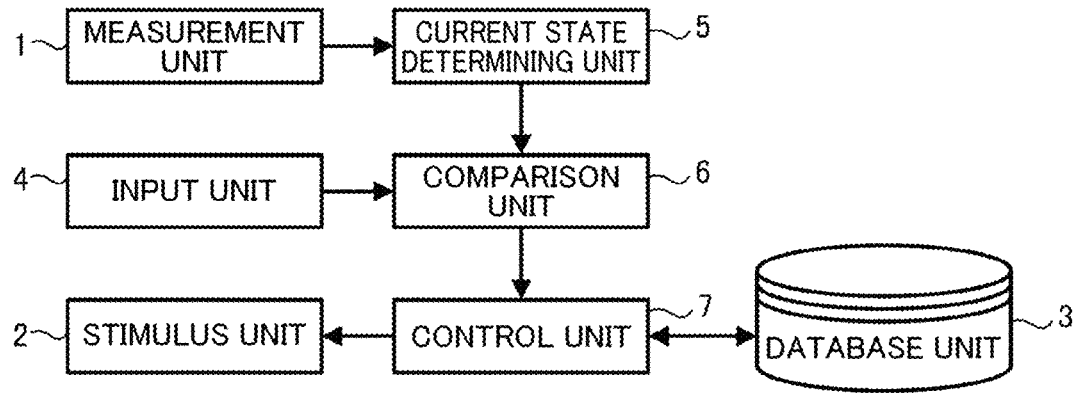
FIG. 1 is a functional block diagram of a living body guidance device according to a first embodiment.

FIG. 1 is a functional block diagram of a living body guidance device according to a first embodiment. The living body guidance device includes a measurement unit 1, a stimulus unit 2, a database unit 3, an input unit 4, a current state determining unit 5, a comparison unit 6 and a control unit 7.

The measurement unit 1 is worn on a user who is a measurement target, and can measure biometric information of the user at regular time intervals. The measurement unit 1 may be, for example, a myoelectric sensor for acquiring muscle activity as an index of movement. The myoelectric sensor is a sensor used to detect muscle activity that is deeply related to the movement as proposed in, for example, "RIZAP×GUNZE's cutting-edge training wear 'Myoden WEAR' is launched, scientifically analyzing and learning correct muscle movement to further improve training performance" [Online], Sep. 25, 2017, PRESS RELEASE, RIZAP Group Inc. [retrieved on May 21, 2019], Internet <URL: https://www.rizapg roup.com/wp-content/uploads/2017/08/pr-20170925-01.pdf>.

The stimulus unit 2 is installed in contact with the user's body and can present a tactile stimulus to the user. The stimulus unit 2 may be any object as long as its properties (for example, shape and/or hardness) can be dynamically controlled in order to apply a tactile stimulus to the user.

The database unit 3 has the relationship between the tactile stimulus presented by the stimulus unit 2 and the biometric information according to the tactile stimulus of the stimulus unit 2 recorded. That is, the database unit 3 may have a database in which kinds of muscle activity generated when the object (the stimulus unit 2) worn on the user has different properties are linked.

The input unit 4 can set target biometric information which is target biometric information to be realized. For example, the muscle activity that the user wants to realize can be set as target muscle activity.

The current state determining unit 5 can estimate current biometric information, which is biometric information of the user at a current point, based on the measurement result from the measurement unit 1. For example, the current state determining unit 5 can estimate muscle activity at a current point based on the value from the myoelectric sensor that is the measurement unit 1. The current state determining unit 5 may estimate biometric information measured by the measurement unit 1 in a first period, for example, a period of one step completed immediately before, as current biometric information in a second period following the first period, that is, a period of the next step starting therefrom.

The comparison unit 6 can estimate the difference between the target biometric information set by the input unit 4 and the current biometric information estimated by the current state determining unit 5.

When the comparison unit 6 estimates that there is a difference, the control unit 7 can control the tactile stimulus presented by the stimulus unit 2 based on the relationship recorded in the database unit 3 so that the difference is reduced, and can guide the user so that current biometric information approaches target biometric information. For example, the control unit 7 can search the database unit 3 for the properties of the stimulus unit 2 that can realize muscle activity closer to the target than the current one based on the difference between the current point muscle activity and target muscle activity. Then, the control unit 7 can dynamically control the stimulus unit 2 so that properties of the search result are realized.

The living body guidance device can repeatedly operate at least the measurement unit 1, the current state determining unit 5, the comparison unit 6, the control unit 7 and the stimulus unit 2 until target biometric information is realized, for example, a change in target muscle activity is realized or until current biometric information does not change, for example, muscle activity does not change. Realization of the target biometric information means that the difference between the target biometric information estimated by the comparison unit 6 and current biometric information is eliminated.

In such a living body guidance device, the stimulus unit 2 of which properties (for example, a shape, a hardness, etc.) dynamically change is worn on the user, and thus applies a tactile stimulus to the user, and encourages the user to spontaneously change the movement. Thereby, the user does not hesitate about how to move his or her body, and can receive assistance to change the movement to a different movement that does not depend on the current movement according to the situation of the user and changes in the surrounding environment as long as the user can move comfortably without adding external power. In addition, it is expected that the user can learn how to move by repeatedly experiencing the target movement that the user wants to realize, and can eventually achieve the target movement without using this living body guidance device. For example, focusing on muscle activity as an index of movement, it is possible to change muscle activity to target muscle activity that the user wants to realize.

Hereinafter, a specific configuration of a living body guidance device according to the first embodiment will be described. As an example, an example in which biometric information is a myoelectric potential which is an index of foot muscle activity and the myoelectric potential is changed by an insole of which hardness changes dynamically will be described.

Figure 2:
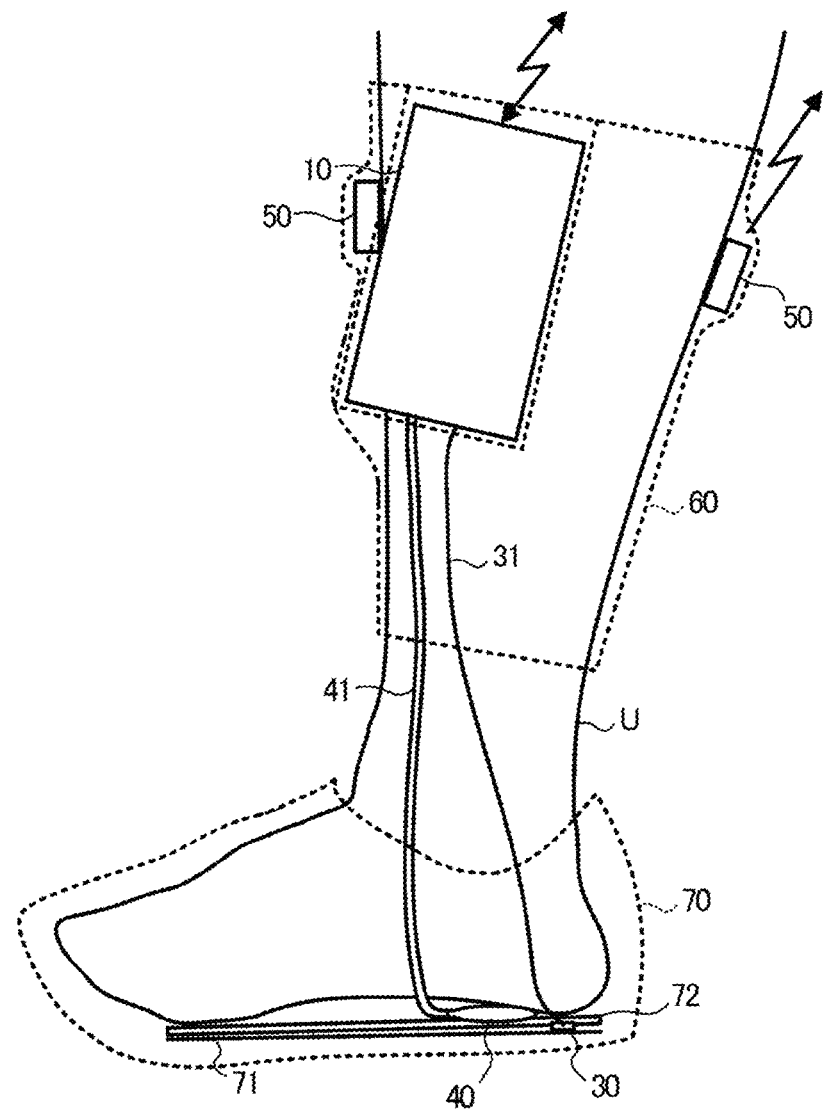
FIG. 2 is a diagram showing an example of a living body guidance device worn by a user.
Figure 3:
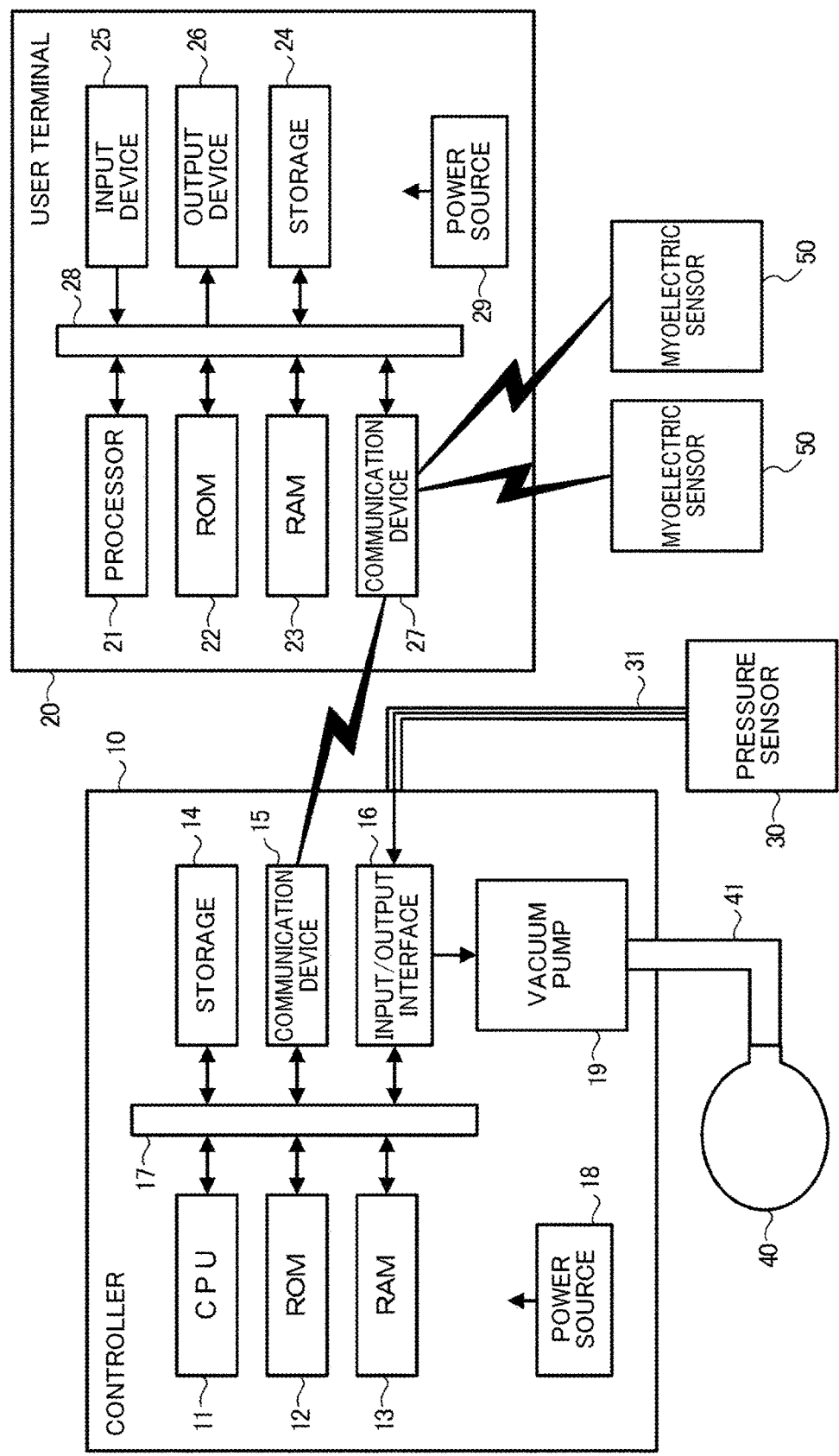
FIG. 3 is a block configuration diagram of a living body guidance device.

FIG. 2 is a diagram showing an example in which a living body guidance device is worn on a user U, and FIG. 3 is a block configuration diagram of the living body guidance device.

A living body guidance device according to the present embodiment can include a controller 10, a user terminal 20, a pressure sensor 30, a bag 40 and a myoelectric sensor 50. Here, for each of the left and right feet of the user U, one controller 10, one pressure sensor 30, one bag 40 and two myoelectric sensors 50 can be used. In FIG. 2 and FIG. 3, only one leg is shown for simplification of the drawings.

The controller 10 and the myoelectric sensor 50 are worn on the user U. For example, the myoelectric sensor 50 can be worn by, for example, being attached to the tibialis anterior muscles and gastrocnemius muscles of the user U's left and right feet. The controller 10 can be attached to the calf by being inserted into a calf supporter 60 for the user U's left and right feet.

The user terminal 20 may be held by the user U or may be disposed away from the user U. When the user terminal 20 is disposed away from the user U, it can be set to be within a distance at which wireless communication is possible with the controller 10 and the myoelectric sensor 50 worn on the user U. Of course, this does not apply when the user terminal 20 is connected to the controller 10 and the myoelectric sensor 50 via a wire.

The pressure sensor 30 and the bag 40 can be attached to a shoe 70 worn on the user U. The pressure sensor 30 can be attached to a heel part between an intermediate bottom 71 and an insole 72 of the shoe 70. The bag 40 may be attached to any location on the shoe 70 as an insole. In the example of FIG. 2, the bag 40 is attached to the front of the heel part on the insole 72 of the shoe 70. The pressure sensor 30 is connected to the controller 10 by a wiring 31, and the bag 40 can be connected to the controller 10 via a pipe 41.

The controller 10 includes a central processing unit (CPU) 11, a ROM 12, a RAM 13, a storage 14, a communication device 15, and an input/output interface 16. These components are connected to each other via a system bus 17 and are operated when power is supplied from a power source 18. A vacuum pump 19 and the pressure sensor 30 are connected to the input/output interface 16.

The CPU 11 is a processor that controls various operations of the controller 10. The ROM 12 records a startup program and the like. The RAM 13 functions as a main storage device of the CPU 11. The storage 14 stores various programs such as a control program used in the CPU 11 and an arithmetic program that executes various arithmetic operations, parameters, and the like. A non-volatile memory such as a flash memory can be used as the storage 14. Various programs such as a control program, parameters, and the like may be stored in the ROM 12, and in this case, the storage 14 may not be provided. The CPU 11 controls operations of the controller 10 by executing various programs in response to a signal received from the communication device 15 or an input signal from the input/output interface 16.

The communication device 15 includes, for example, a wireless communication interface unit, and can transmit and receive various pieces of information to and from an external device such as the user terminal 20. For example, an interface using a low power wireless data communication standard such as a wireless LAN or Bluetooth (registered trademark) can be used as the wireless interface. In this example, the communication device 15 performs wireless communication with the user terminal 20, but it may perform wired communication. For example, a Universal Serial Bus (USB) interface can be used as the wired interface.

The input/output interface 16 has a plurality of input/output pins for inputting and outputting digital data and an analog signal. The input/output interface 16 can connect the wiring 31 of the pressure sensor 30 and receive a sensor value of the pressure sensor 30, that is, a measurement data input. In addition, the input/output interface 16 can connect a control wiring of the vacuum pump 19 and apply drive control data from the CPU 11 to the vacuum pump 19. That is, the CPU 11 can acquire the sensor value of the pressure sensor 30 and perform drive control on the vacuum pump 19 via the input/output interface 16. Here, the drive control can be, for example, pulse width modulation (PWM) control (a designation of a duty ratio).

While the power source 18 is built into the controller 10, a small external power source such as a mobile battery may be connected and used. When a mobile battery is used, like the controller 10, the mobile battery can be inserted into the calf supporter 60 and attached to the calf of the user U.

The vacuum pump 19 can be connected to the bag 40 via the pipe 41.

For example, a microcomputer (for example, Arduino Leonardo) with a wireless module (for example, RBT-001) can be used as the controller 10. For example, a small air pump such as SC3101PM can be used as the vacuum pump 19.

The pressure sensor 30 measures the applied pressure and outputs it as 8-bit (value of 0 to 255) measurement data. For example, a small sensor such as FSR402 can be used as the pressure sensor 30.

The bag 40 is a 7-inch balloon containing 10 g of coffee powder therein. The bag 40 becomes hard by the vacuum pump 19 sucking out air in the bag 40. This is due to a "jamming transition phenomenon" which is a phenomenon in which, when the density of a powder is low, the powder has properties similar to those of a liquid, but when the density increases and exceeds a certain value, the powder has properties similar to those of a solid. The powder to be put into the bag 40 is not limited to coffee powder, and other particles such as couscous (granular powder food made from wheat flour) and sand can be used.

The user terminal 20 is an information processing device such as a personal computer (PC) or a smartphone. The user terminal 20 includes a processor 21, a ROM 22, a RAM 23, a storage 24, an input device 25, an output device 26, and a communication device 27. These components are connected to each other via a system bus 28, and are operated when power is supplied from a power source 29.

The processor 21 may be an integrated circuit such as a CPU. The ROM 22 records information used for operations of the processor 21. The RAM 23 functions as a main storage device of the processor 21. The storage 24 stores a control program used in the processor 21, various application programs including a living body guidance program according to one embodiment, parameters and the like. Various application programs may be downloaded in the storage 24 from a web server (not shown) via a network and the communication device 27. Various application programs that are recorded in a recording medium (not shown) such as a disk medium or a memory medium are provided and may be read from a recording medium and recorded in the storage 24. The processor 21 controls operations of the user terminal 20 according to the program stored in the storage 24. A processor other than a CPU, for example, an application specific integrated circuit (ASIC), a field programmable gate array (FPGA), or the like, may be used as the processor 21.

The input device 25 includes an input unit such as a keyboard, a mouse, and a touch panel disposed on a display screen of a liquid crystal display as the output device 26. In addition, the input device 25 can include a multimedia information input unit such as a microphone and a camera. By operating the input device 25, an input signal is input to the processor 21 via the system bus 28.

The output device 26 includes an external display device such as a liquid crystal display or a display unit such as a liquid crystal display of the user terminal 20. An output signal is transmitted to the output device 26 from the processor 21 via the system bus 28.

The communication device 27 includes, for example, one or more wired or wireless communication interface units, and can communicate with an external device via an external communication network such as a network. For example, a wired LAN or a USB interface is used as the wired interface, and an interface using low power wireless data communication standards, for example, a wireless LAN or Bluetooth, is used as the wireless interface. In this example, a device including the controller 10 and the plurality of myoelectric sensors 50 attached to the left and right feet can be used as an external device that communicates with the communication device 27. The communication device 27 may perform wired communication with each controller 10 and each myoelectric sensor 50 as described above, but preferably performs wireless communication in consideration of ease of walking of the user U.

The myoelectric sensor 50 measures a myoelectric potential that is a potential generated according to muscle tension. For example, a Trigno sensor that measures a myoelectric potential and wirelessly transmits an electromyography (EMG) signal as its measurement data can be used as the myoelectric sensor 50.

In the above configuration, the vacuum pump 19 and the bag 40 can function as the stimulus unit 2. The database unit 3 can be provided in the storage 24 of the user terminal 20. The processor 21 and the input device 25 can function as the input unit 4. The processor 21 can function as the current state determining unit 5 and the comparison unit 6. The processor 21 and the CPU 11 of the controller 10 can function as the control unit 7.

In the database unit 3 provided in the storage 24 of the user terminal 20, it is possible to register a link related to a level of a myoelectric potential that is generated according to a level of hardness of an object worn on the user U, in this example, the bag 40, in advance. Biometric information linked to the hardness may be a feature value of the myoelectric potential in addition to the myoelectric potential itself. As the feature value of the myoelectric potential, for example, an integral value ([V]) of a myoelectric potential which is an index of an amount of muscle activity, is conceivable.

FIG. 4 is a diagram showing a content example of the database unit 3. Here, the database unit 3 has a hardness-iEMG table in which the hardness of the bag 40 as an example of dynamically changing properties and an integral value of a myoelectric potential (hereinafter referred to as an iEMG) for each step as an example of the feature value of the myoelectric potential as a target that changes are linked and registered. As a method of registration, for example, it is conceivable to use data obtained in the user experiment in advance. That is, an experiment in which various levels of the hardness of the bag 40 are presented to a plurality of users, and an iEMG obtained for each hardness is measured is performed in advance, and a hardness-iEMG table is created. Here, in FIG. 4, two types of hardness, "hard" and "soft" are registered, but of course, three or more types may be registered. In addition, the prescribed hardness (initial value) of the bag 40 can be stored as a part or a parameter of the living body guidance program in the storage 24. The prescribed hardness of the bag 40 may be registered in the database unit 3.

In addition, in the database unit 3 provided in the storage 24, it is possible to register a link related to a level of hardness that the bag 40 has according to a drive amount of the vacuum pump 19, in advance.

FIG. 5 is a diagram showing a content example of the database unit 3. Here, the database unit 3 has a hardness-drive amount table in which the hardness of the bag 40 as an example of dynamically changing properties and a drive amount of the vacuum pump 19 for realizing the hardness are linked and registered. An appropriate value of the drive amount is registered according to properties of the bag 40 itself such as the size of the bag 40 that is used and properties of the content of the bag 40. Here, in FIG. 5, the drive amount is represented by a suction pressure of the vacuum pump 19, but may be represented by other values such as a rotation speed of the motor of the vacuum pump 19.

Hereinafter, operations of the living body guidance device having the above configuration will be described. The living body guidance device of the present embodiment targets the walking user U and acts on the next step according to one step completed immediately before. In the present embodiment, one step is regarded as a step from when the heel of one foot touches the ground until the heel of that foot touches the ground again through a stance phase and a swing phase. That is, the living body guidance device of the present embodiment is a device that regards a value obtained by adding all of myoelectric potentials obtained from when the heel of one foot touches the ground until it touches the ground again as a feature value of the myoelectric potential, and guides the value of the walking user U to be changed by dynamically changing the hardness of the insole.

Figure 6:
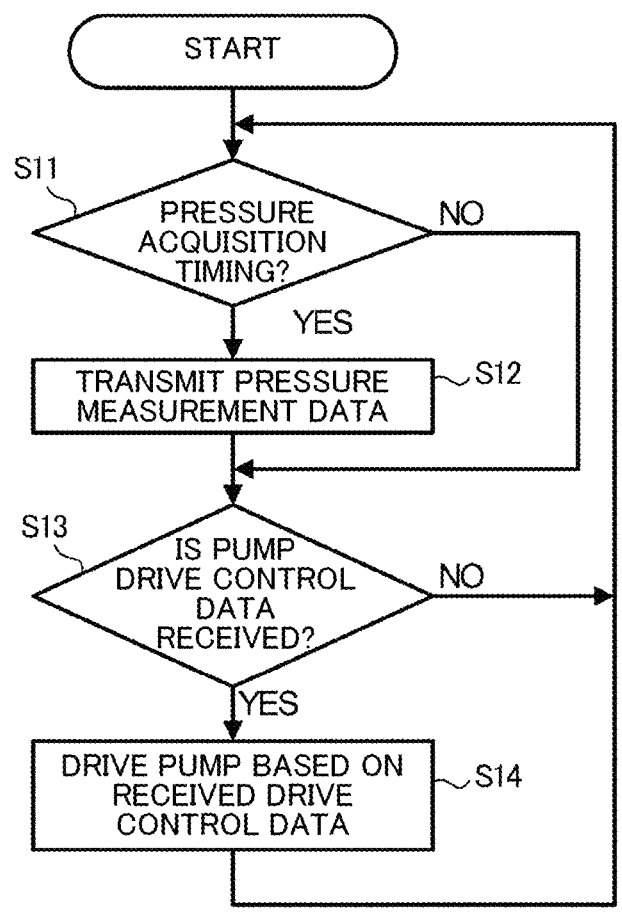
FIG. 6 is an operation flowchart of a CPU provided in a controller.

FIG. 6 is an operation flowchart of the CPU 11 provided in the controller 10. A program causing the CPU 11 to perform this operation is stored in the storage 14, and when the CPU 11 executes the program, the operation as shown in FIG. 6 can be performed.

When the controller 10 is activated, the CPU 11 determines in Step S11 whether it is a pressure acquisition timing at which measurement data of the pressure sensor 30 is acquired. In the present embodiment, for example, measurement data can be set to be acquired 10,000 times per second. Of course, the present invention is not limited to this number of times. When it is determined that it is not a pressure acquisition timing, the CPU 11 advances the process to Step S13 to be described below. When it is determined that it is a pressure acquisition timing, in Step S12, the CPU 11 transmits the measurement data from the pressure sensor 30 captured via the input/output interface 16 to the user terminal 20 by the communication device 15.

The CPU 11 determines in Step S13 whether drive control data of the vacuum pump 19 has been received from the user terminal 20 by the communication device 15. When it is determined that the drive control data has not been received, the CPU 11 repeats the process from Step S11. When it is determined that the drive control data has been received, the CPU 11 drives the vacuum pump 19 via the input/output interface 16 based on the received drive control data in Step S14. Then, the CPU 11 advances the process to Step S11.

Figure 7:
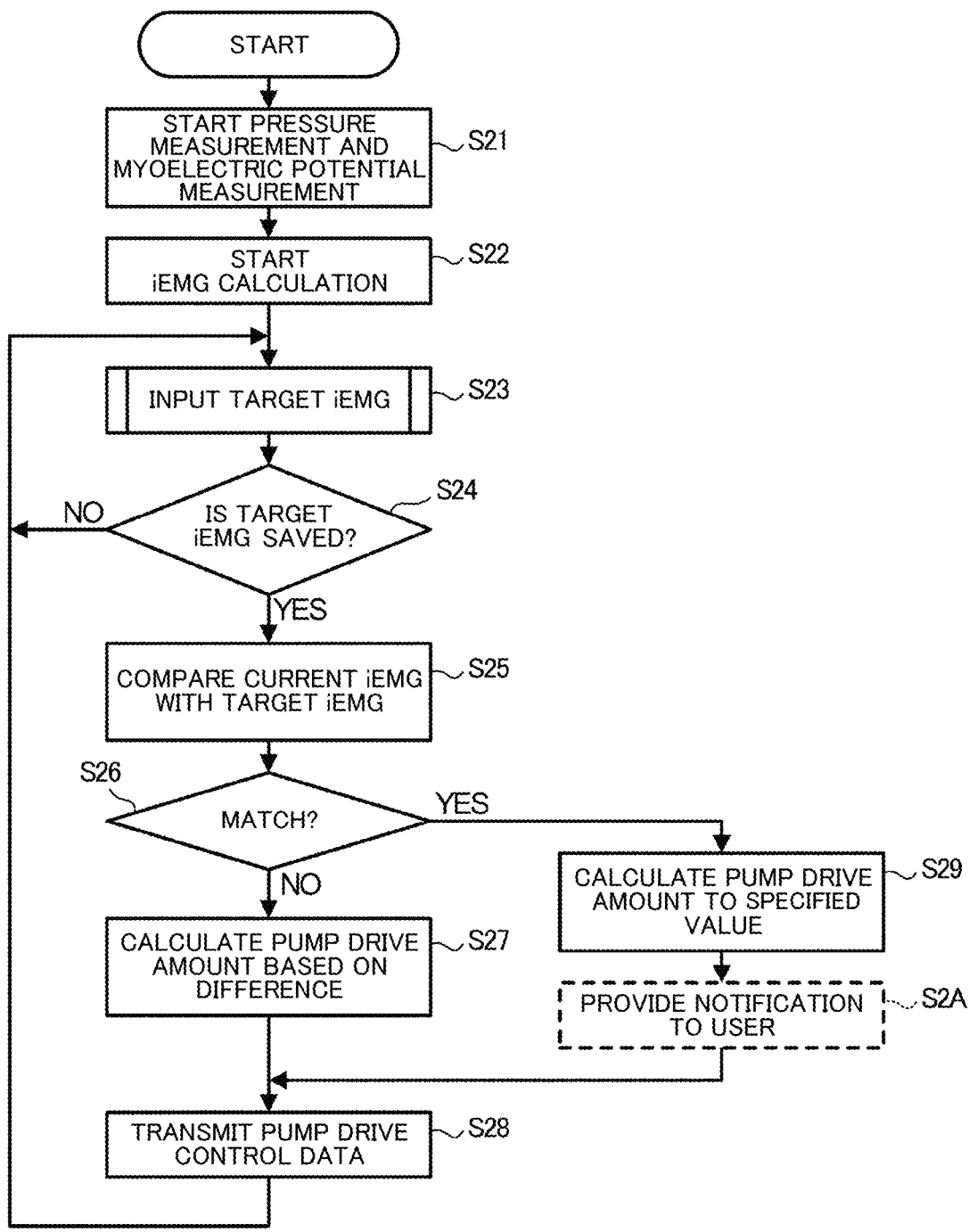
FIG. 7 is a main operation flowchart of a processor provided in a user terminal, which executes a living body guidance program according to the first embodiment.

FIG. 7 is a main operation flowchart executed by the processor 21 included in the user terminal 20. The living body guidance program according to the first embodiment causing the processor 21 to perform the operation is stored in the storage 24, and the processor 21 can execute the living body guidance program to perform the operation as shown in FIG. 7.

When the user U instructs execution of the living body guidance program using the input device 25, the processor 21 starts pressure measurement and myoelectric potential measurement in Step S21. In Step S22, the processor 21 starts iEMG calculation.

Figure 8:
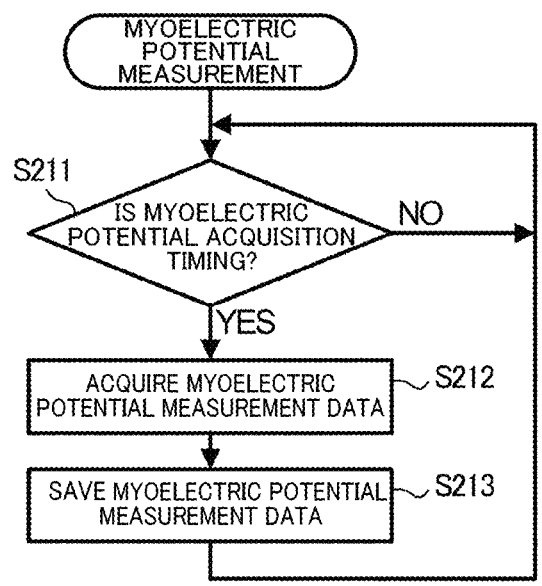
FIG. 8 is an operation flowchart of a myoelectric potential measuring process performed by the processor.

FIG. 8 is an operation flowchart of a myoelectric potential measuring process performed by the processor 21. The myoelectric potential measuring process can be executed by the processor 21 in parallel with the main operation shown in FIG. 7. In Step S211, the processor 21 determines whether it is a myoelectric potential acquisition timing at which measurement data of the myoelectric sensor 50 is acquired. In the present embodiment, for example, myoelectric potential measurement data can be set to be acquired 2,000 times per second. Of course, the present invention is not limited to this number of times. When it is determined that it is not a myoelectric potential acquisition timing, the processor 21 repeats the determination of Step S211. When it is determined that it is a myoelectric potential acquisition timing, the processor 21 acquires myoelectric potential measurement data which is measurement data from each myoelectric sensor 50 via the communication device 27 in Step S212. The processor 21 saves the acquired myoelectric potential measurement data in the RAM 23 together with a time stamp indicating the acquisition time in Step S213. Then, the processor 21 advances the process to Step S211.

Figure 9:
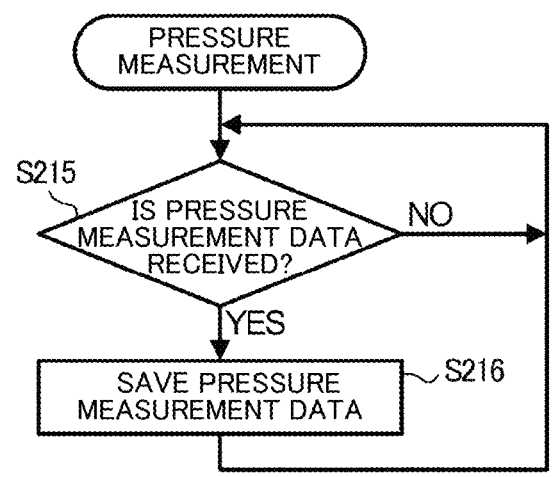
FIG. 9 is an operation flowchart of a pressure measuring process performed by the processor.

FIG. 9 is an operation flowchart of a pressure measuring process performed by the processor 21. The pressure measuring process can be executed by the processor 21 in parallel with the main operation shown in FIG. 7. In Step S215, the processor 21 determines whether pressure measurement data, which is the measurement data of the pressure sensor 30 transmitted from the controller 10 by the communication device 27, has been received. As described above, in the present embodiment, for example, the measurement data of the pressure sensor 30 is transmitted from the controller 10 to the user terminal 20 10,000 times per second. When it is determined that the pressure measurement data has not been received, the processor 21 repeats the determination of Step S215. When it is determined that the pressure measurement data has received, the processor 21 saves the received pressure measurement data in the RAM 23 together with a time stamp indicating the acquisition time in Step S216. Then, the processor 21 advances the process to Step S215.

Figure 10:
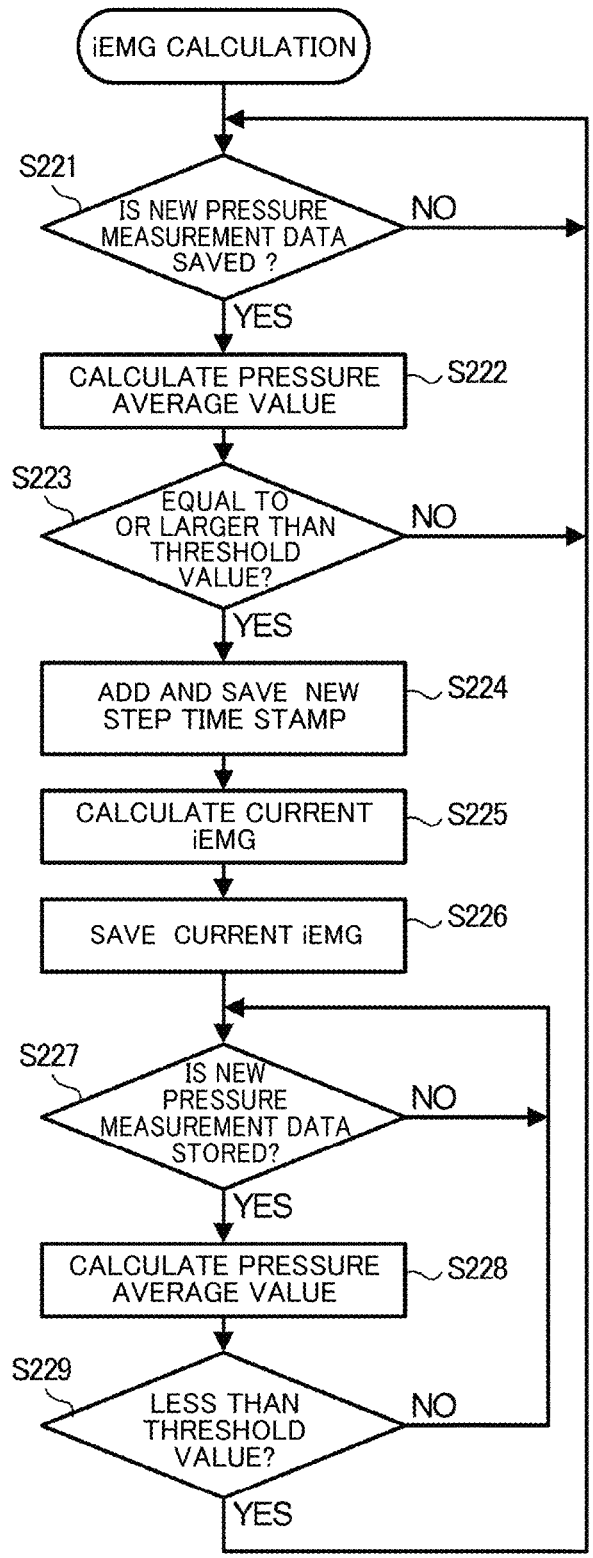
FIG. 10 is an operation flowchart of an iEMG calculation process performed by the processor.

FIG. 10 is an operation flowchart of an iEMG calculation process performed by the processor 21. The iEMG calculation process can be executed by the processor 21 in parallel with the main operation shown in FIG. 7. The iEMG calculation process is a process in which measurement data of the myoelectric sensor 50 and the pressure sensor 30 saved in the RAM 23 is used to calculate an iEMG (hereinafter referred to as a current iEMG) of one step of the walking user U completed immediately before.

In Step S221, the processor 21 determines whether new pressure measurement data is saved in the RAM 23. When it is determined that new pressure measurement data is not saved, the processor 21 repeats the determination of Step S221. When it is determined that new pressure measurement data is saved, the processor 21 calculates a pressure average value in Step S222. The pressure average value can be an average value of pressure measurement data of the last 10 times including new pressure measurement data. Of course, the present invention is not limited to the average of these 10 times.

Figure 11A:
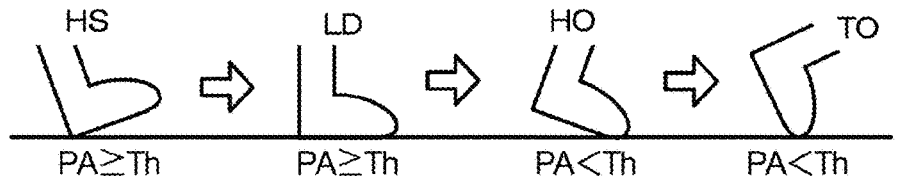
FIG. 11A is a schematic view for explaining the relationship between a pressure average value and a threshold value.
Figure 11B:
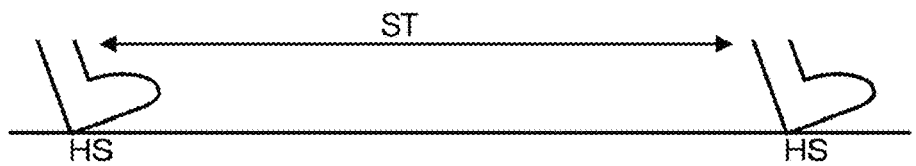
FIG. 11B is a schematic view for explaining one step of a user.

In Step S223, the processor 21 determines whether the calculated pressure average value is equal to or larger than the threshold value. FIG. 11A is a schematic view for explaining the relationship between a pressure average value PA and a threshold value Th, and FIG. 11B is a schematic view for explaining one step of the user U. The threshold value Th is set to a value at which the pressure average value PA is equal to or larger than the threshold value Th in a heel contact state HS in which the user U's heel touches the ground. The pressure average value PA is equal to or larger than the threshold value Th in the heel contact state HS, the sole contact state in which the sole of the user U touches the ground, and the landing state LD including a middle standing phase. Then, in the heel takeoff state HO in which the heel takes off, the pressure average value PA becomes a value smaller than the threshold value Th. In the toe takeoff state TO in which the toes take off in the heel takeoff state HO, and additionally, in the swing phase, the pressure average value PA becomes less than the threshold value Th. A period from a certain heel contact state HS to the next heel ground state HS is one step ST of walking of the user U. The determination process in Step S223 is a process of determining whether the heel of the foot of the user U has touched the ground, that is, one step ST of the user U has started. When it is determined that the calculated pressure average value AP is not equal to or larger than the threshold value Th, the processor 21 advances the process to Step S221, and repeats the above process. When it is determined that the pressure average value PA is equal to or larger than the threshold value Th, the processor 21 advances the process to the next process in Step S224. The processor 21 regards a time at which the pressure average value PA changes from a value smaller than the threshold value Th to a value equal to or larger than the threshold value Th as a time at which the heel of the foot touches the ground, that is, a time at which one step of the user starts, and additionally saves the time in the RAM 23 as a new step start time stamp.

In Step S225, the processor 21 calculates a current iEMG which is an iEMG of one step completed immediately before. This is a process in which all of the values of myoelectric potential measurement data that is measured between the time indicated by a new step start time stamp additionally saved in the RAM 23 and the time indicated by one step start time stamp saved one time before and saved in the RAM 23 are added and the addition result is used as a current iEMG. The processor 21 saves the calculated current iEMG in the RAM 23 in Step S226.

The processor 21 determines in Step S227 whether new pressure measurement data is saved in the RAM 23. When it is determined that new pressure measurement data is not saved, the processor 21 repeats the determination of Step S227. When it is determined that new pressure measurement data is saved, the processor 21 calculates a pressure average value PA in Step S228 in the same manner as in Step S222. The processor 21 determines in Step S229 whether the calculated pressure average value PA is less than the threshold value Th. That is, it is determined whether the walking state of the user U is a heel takeoff state HO. When it is determined that the calculated pressure average value PA is not less than the threshold value Th, that is, is equal to or larger than the threshold value Th, the processor 21 advances the process to Step S227, and repeats the above process. When it is determined that the pressure average value PA is less than the threshold value Th, the processor 21 advances the process to Step S221 and repeats the above process.

In this manner, the myoelectric sensor 50 and the processor 21 realize the function of the measurement unit 1 that calculates an iEMG which is biometric information from a plurality of myoelectric potentials measured by the myoelectric sensor 50 in one step period. Then, the processor 21 realizes the function of the current state determining unit 5 that estimates an iEMG which is the biometric information calculated in the one step period completed immediately before, which is the first period, as a current iEMG which is current biometric information in the period of the next step, which is the second period following the first period, and continues calculation of the current iEMG.

Figure 12:
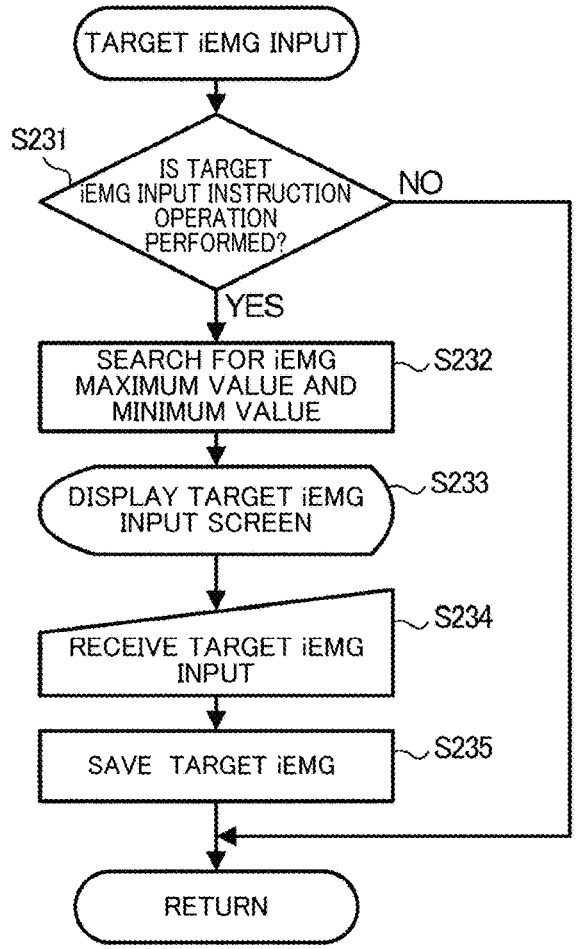
FIG. 12 is an operation flowchart of a target iEMG input subroutine.

The main operation of FIG. 7 will be referred to again. In Step S23, the processor 21 executes an operation of a target iEMG input subroutine for the user U to set target biometric information which is the value of the ideal iEMG (hereinafter referred to as a target iEMG) that the user U wants to realize. FIG. 12 is an operation flowchart of the target iEMG input subroutine. In Step S23, the processor 21 determines whether an input instruction operation of the target iEMG from the user U using the input device 25 has been performed. When it is determined that no target iEMG input instruction operation has been performed, the processor 21 ends the operation of the target iEMG input subroutine and returns to the main operation of FIG. 7. In Step S24, the processor 21 determines whether the target iEMG is saved in the RAM 23 according to the operation of the target iEMG input subroutine. When it is determined that the target iEMG is not saved, the processor 21 advances the process to Step S23, and receives an input of the target iEMG. In this manner, the processor 21 waits for the target iEMG to be input from the user U.

When it is determined in Step S231 that the target iEMG input instruction operation has been performed, the processor 21 searches for a maximum value and a minimum value from the past current iEMG that has been continuously saved in the RAM 23 according to the iEMG calculation process described with reference to FIG. 10 in Step S232. In Step S233, the processor 21 displays a target iEMG input screen on the output device 26. Although the target iEMG input screen is not particularly shown, a value between the maximum value and the minimum value of the searched iEMG can be displayed as an input range of the target iEMG. In Step S234, the processor 21 receives the target iEMG input by the user U using the input device 25. For example, the target iEMG may be limited to a value between the maximum value and the minimum value of the searched iEMG. The processor 21 saves the input target iEMG value in the RAM 23 in Step S235. In this manner, the processor 21 and the input device 25 can realize functions of the input unit 4. Then, the processor 21 ends the operation of the target iEMG input subroutine and returns to the main operation of FIG. 7.

In this manner, when the target iEMG is set by the user U, the processor 21 determines that the target iEMG is saved in Step S24. In this case, the processor 21 compares the current iEMG at a current point saved in the RAM 23 with the set target iEMG in Step S25. In Step S26, the processor 21 determines whether comparison results match. In this manner, the processor 21 can realize functions of the comparison unit 6.

When it is determined that the comparison results between the current iEMG and the target iEMG do not match, the processor 21 calculates a drive amount of the vacuum pump 19 based on the difference between them in Step S27. That is, the processor 21 searches the hardness-iEMG table of the database unit 3 for the hardness of the bag 40 that can realize an iEMG closer to the target iEMG, and calculates a drive amount of the vacuum pump 19 for making the bag 40 have the hardness. For example, when the target iEMG is larger than the current iEMG, the processor 21 can search the hardness-iEMG table for the hardness that can realize an iEMG larger than the current iEMG. On the other hand, when the target iEMG is smaller than the current iEMG, the processor 21 can search the hardness-iEMG table for the hardness that can realize an iEMG smaller than the current iEMG.

As a specific example, for example, when the target iEMG is 40 [μV] and the current iEMG is 60 [μV], the target iEMG is smaller than the current iEMG, and the difference between them (target iEMG-current iEMG) is −20 [μV]. Here, when the content of the hardness-iEMG table of the database unit 3 is as shown in the example of FIG. 4, since the value of the iEMG corresponding to "hard" searched from the hardness-iEMG table is 30 [μV], the difference from the current iEMG (hard iEMG-current iEMG) is −30 [μV]. Since the value of the iEMG corresponding to "soft" searched from the hardness-iEMG table is 70 [μV], the difference from the current iEMG (soft iEMG-current iEMG) is 10 [μV]. Between these −30 [μV] and 10 [μV], since −30 [μV] is closer to the difference of −20 [μV] between the target iEMG and the current iEMG (small difference), "hard" is searched for as the hardness of the bag 40 that realizes it. The processor 21 calculates a drive amount of the vacuum pump 19 for setting the bag 40 in this "hard" state. The drive amount of the vacuum pump 19, for example, the drive amount of the vacuum pump 19 corresponding to the hardness "hard" of the bag 40 can be calculated from, for example, a relationship between the drive amount of the vacuum pump 19 and the hardness of the bag 40 separately determined and registered as a hardness-drive amount table in the database unit 3.

The drive amount of the vacuum pump 19 may be calculated by a method other than the above method. For example, when the target iEMG is 40 [μV] and the current iEMG is 60 [μV], the hardness-iEMG table in the database unit 3 is searched for an iEMG closer to the target iEMG, and thus the hardness of the bag 40 corresponding to the iEMG is obtained. In this case, the hardness of the bag 40 corresponding to an iEMG closer to the target iEMG is "hard" in which the iEMG is 30 [μV]. The processor 21 calculates a drive amount of the vacuum pump 19 corresponding to the hardness "hard" of the bag 40 from, for example, a relationship between the drive amount of the vacuum pump 19 and the hardness of the bag 40 separately determined and registered as a hardness-drive amount table in the database unit 3. In this case, when the degree of the hardness of the bag 40 in which the iEMG is the same as the target iEMG of 40 [μV] is not defined, based on the relationship between the iEMG, the hardness of the bag 40, and the drive amount of the vacuum pump 19, the drive amount of the vacuum pump 19 which is the target iEMG may be obtained by interpolating numerical values appropriately.

In Step S28, the processor 21 transmits pump drive control data indicating the calculated drive amount of the vacuum pump 19 to the controller 10 via the communication device 27. The pump drive control data may be data indicating a value (drive amount) of the vacuum pump 19 corresponding to the target hardness of the bag 40 or may be data indicating a relative value (drive amount) from the current state of the vacuum pump 19. If the drive amount of the vacuum pump 19 is specified as a relative value (drive amount), for example, when the hardness of the bag 40 is "hard", if the current state of the bag 40 is not the prescribed hardness (initial state) nor the soft state, but is already the hard state, the drive amount of the vacuum pump 19 indicating pump drive control data becomes zero. When the current state of the bag 40 is not a "hard" state, the processor 21 can use data indicating the drive amount of the vacuum pump 19 for changing the bag 40 from the current state to the hard state as pump drive control data. The CPU 11 of the controller 10 receives the pump drive control data by the communication device 15 and PWM-controls the vacuum pump 19 according to the drive amount of the vacuum pump 19 indicated by the pump drive control data. Thereby, the bag 40 that functions as the stimulus unit 2 can realize the hardness instructed by the processor 21. In this manner, the processor 21 and the CPU 11 can realize the function as the control unit 7.

The processor 21 advances the process to Step S23 and repeats the above process.

Figure 13:
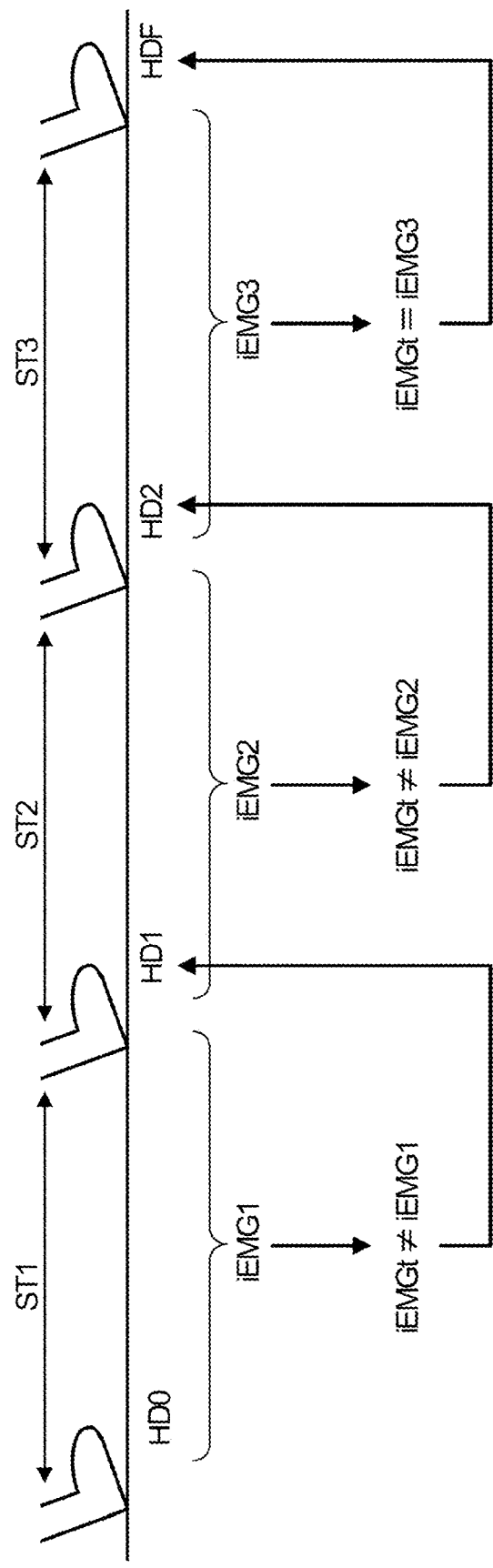
FIG. 13 is a schematic view for explaining operations of the living body guidance device.

FIG. 13 is a schematic view for explaining operations of the living body guidance device. When walking of the first step ST1 of the user U ends, an iEMG1 which is an integral value of myoelectric potentials measured during walking of the first step ST1 is calculated, and compared with the iEMGt which is the target iEMG. When the iEMG1 does not match the iEMGt, the hardness of the bag 40 is adjusted based on the difference between them. That is, the hardness is changed from HD0 which is the hardness during the first step ST1 to HD1 which is the hardness during the second step ST2. Depending on the hardness state of HD0, HD0=HD1 may be possible.

Similarly, when walking of the second step ST2 of the user U ends, when walking of the third step ST3 of the user U ends, . . . , iEMG2, iEMG3, . . . are calculated, and compared with iEMGt, and the hardness of the bag 40 is adjusted according to the result.

For example, when walking of the third step ST3 ends, if the iEMG3 matches the iEMGt (iEMGt=iEMG3), the processor 21 determines that comparison results of the current iEMG and the target iEMG match in Step S26. In this case, the processor 21 calculates a drive amount of the vacuum pump 19 to the default value in Step S29. That is, the processor 21 calculates a drive amount of the vacuum pump 19 for making the hardness of the bag 40 be a prescribed hardness. In Step S28, the processor 21 transmits pump drive control data indicating the calculated drive amount of the vacuum pump 19 to the controller 10 via the communication device 27. Thereby, the CPU 11 of the controller 10 can PWM-control the vacuum pump 19 and set the bag 40 to HDF with a prescribed hardness.

In this manner, the hardness of the bag 40 in the current step depends on the situation of the user U during walking one step before. Therefore, it is preferable to inform the user U in advance that a step one step before in which the default hardness is presented is a target movement. That is, in the present embodiment, if the user U recognizes that the movement of the previous step when the bag 40 reaches the default hardness=target movement, the user U says, "The bag has now reached the default hardness! Please, do the previous step movement!", and takes the movement of the previous step.

Here, when it is detected that the movement matches a target movement, or one step before in which the default hardness of the bag 40 is presented, which is the time when the target movement is achieved, begins, that is, when the previous step is completed, a sound of "dingdong" or the like may be used to explicitly inform the user U regarding which operation is the target movement. This can be realized by adding Step S2A which is a process for that purpose between Step S29 and Step S28, as indicated by the dashed line in FIG. 7. That is, in Step S2A, the processor 21 generates a notification sound to the user U by a speaker (not shown).

According to the first embodiment described above, the processor 21 of the user terminal 20 measures an integral value (iEMG) of myoelectric potentials, which is biometric information of the user U, based on the myoelectric potential measured by the myoelectric sensor 50 in real time. In addition, the bag 40 which is a stimulus unit of which properties such as the hardness can be dynamically changed and which presents a tactile stimulus to the user U is installed in contact with the user U's body. The storage 24 of the user terminal 20 includes the database unit 3 in which relationship between the tactile stimulus presented by the bag 40 and the iEMG caused by the tactile stimulus is recorded in the hardness-iEMG table. When the processor 21 of the user terminal 20 receives the target iEMG input by the user U using the input device 25, and there is a difference between the current iEMG of the user U estimated based on the iEMG of the measurement result and the target iEMG, it calculates a tactile stimulus presented on the bag 40, that is, the hardness, based on the relationship recorded in the hardness-iEMG table, so that the difference is reduced. The processor 21 wirelessly issues an instruction from the user terminal 20 to the controller 10 so that the insole realizes the hardness calculated in this manner. The CPU 11 of the controller 10 PWM-controls the vacuum pump 19 based on the instruction and controls the hardness of the insole by sucking air from the bag 40. When the hardness of the insole is controlled in this manner, the user U is guided so that the current iEMG is closer to the target iEMG.

As described above, when properties of the object worn on the user U's body are dynamically changed, it is possible to apply a tactile stimulus to the user U's body and cause a change in the muscle activity. That is, it is possible to apply a target movement that the user wants to realize, for example, an appropriate and safe tactile stimulus for guiding the user U to perform muscle activity, to the user U. When the muscle activity is changed, for example, the muscle activity of the agonist muscle and the antagonist muscle can be balanced, which may lead to injury prevention and performance improvement. Thereby, the user U can learn target muscle activity that the user wants to realize, and it is expected that the user can eventually realize target muscle activity without using the living body guidance device.

Here, since the destination of the process from Step S28 is set to Step S23, the user U can change the target iEMG at any time.

Modified Examples

The following modified examples can be considered for partial parts of the first embodiment.

Method of Creating Database Unit 3

In the first embodiment, the database unit 3 is created based on the results of actual tests for a plurality of users. For example, the database unit 3 may be created using data obtained from when the user U to be guided wears the myoelectric sensor 50 until the value of the target iEMG is input. For example, before the user U inputs the value of the target iEMG, various levels of the hardness of the bag 40 are presented and the user U is asked to walk, the iEMG obtained in this case is linked to the level of the presented hardness and registered, and thus the database unit 3 can be created.

Target to be Changed

In the first embodiment, the integral value (iEMG) of the myoelectric potential, which is one of feature values of the myoelectric potential, is a target to be changed. Regarding the target to be changed, other feature values of the myoelectric potential, for example, a maximum amplitude ([V]) of the myoelectric potential which is the maximum value of the myoelectric potential in one step, the timing ([%]) during one step of the maximum amplitude of the myoelectric potential, the activity period ([%]) of the myoelectric potential which is a ratio at which the myoelectric potential in one step exceeds a threshold value or more, and the like are considered. In addition, the myoelectric potential itself can be considered as a target to be changed. For example, it is also conceivable to finely change the myoelectric potential itself, such as changing the myoelectric potential at a certain timing (for example, myoelectric potential ([V]) at 50 [%] in one step) to increase, or changing the rate of increase (for example, the difference ([V]) in the myoelectric potential between 50 [%] and 60 [%] in in one step) of the myoelectric potential at a certain timing to be larger.

Target Part to be Changed and Wearing Part

In the first embodiment, the calf of the walking user U is used as a target part to be changed, and the sole is used as a wearing part as the bag 40 of the stimulus unit 2. However, not only the calf and the sole, but also any body part of the user U such as the thighs, arms, and abdomen can be the target part or the wearing part. For example, the user U's thighs during squats, the user U's arms during push-ups, and the user U's abdomen during abdominal exercises and the like can also be the target part or the wearing part.

For example, when squats are performed, the myoelectric sensor 50 is attached to the hamstring of the user U, the bag 40 is attached to the thigh so that movement of the muscle to which the myoelectric sensor 50 is attached is restricted or attached to the sole which is a part of the body that will come into contact with the ground and exerts the strength during the operation. As a specific control method, measurement of an iEMG for one squat operation (from when the thigh is stretched until it is bent and stretched again) continues. When it is desired to increase a load as in muscle training, in the next operation, performing control such that the bag 40 is hardened so that the user can learn how to move muscles that increase the iEMG, and when it is desired to reduce fatigue, performing control such that the bag 40 is softened so that the user can learn how to move muscles that reduce the iEMG and the like can be considered.

When the user U performs push-up, the myoelectric sensor 50 is attached to the triceps of the user U, the bag 40 is attached to the arm so that movement of the muscle to which the myoelectric sensor 50 is attached is restricted or attached to the palm of the hand which is a part of the body that will come into contact with the ground and exerts the strength during the operation, measurement of an iEMG for one push-up operation (from when the arm is stretched unit it is bent and stretched again) continues and the same control as for squats is performed.

When the user U performs abdominal exercise, the myoelectric sensor 50 is attached to the rectus abdominis muscle of the user U, the bag 40 is wrapped around and attached to the abdomen so that movement of the muscle to which the myoelectric sensor 50 is attached is restricted, measurement of an iEMG for one abdominal exercise operation (from when the abdomen is stretched until it is bent and stretched again) continues, and the same control as for squats is performed.

Road Conditions and Temperature During Walking (Surrounding Environment)

In the first embodiment, walking on a flat road is assumed and road conditions during walking are not considered. However, control may be performed in consideration of road conditions during walking. For example, in the case of a slope, control is performed so that the bag 40 of the heel part becomes hard, and thus climbing becomes easier and control is performed so that a kind of walking method that makes walking on the slope easy is presented to the user U. On a bumpy road such as a mountain road, control is performed so that the entire bag 40 is softened, and thus an impact due to the bump can be absorbed, and control is performed so that a kind of walking that makes walking on the mountain road easy is presented. In this manner, it is conceivable to implement a control method that allows the user U to learn walking according to the surrounding environment.

In addition, the temperature during walking may be considered. For example, it is considered that, when the temperature is high, the bag 40 is controlled such that it becomes hard and thus the iEMG is small in order to demonstrate walking that reduces the burden of walking, and when the temperature is low, the bag 40 is controlled such that it becomes soft and thus the iEMG is large in order to demonstrate walking that increases the amount of muscle activity in order to warm the body.

Properties that Dynamically Change and Realizing Method

In the first embodiment, the hardness is a target as an example of properties that is dynamically changed. However, not only the hardness, but also the shape, the temperature, the pressure, and the like can be the properties to be dynamically changed. In addition, these plurality of properties may be combined and presented to the user U. As a method of realizing each property, any method can be used as long as each property is changed in a programmable manner. An example of each property is shown below.

Hardness

In the first embodiment, the density in the bag 40 is changed using a physical phenomenon called jamming transition and thus the hardness of the bag 40 is dynamically changed. However, it is also conceivable that the hardness of the bag 40 is changed in a programmable manner using an object of which hardness changes depending on, for example, the water amount and water pressure (dilatant fluid), the temperature (special plastic), the electricity (electrorheological fluid), or the magnetic force (magnetic fluid), instead of the jamming transition. Examples of the object of which hardness changes depending on the amount of water include a dilatant fluid. Specifically, the hardness of the bag 40 can be changed by programmatically controlling the amount of water in a mixture containing water and potato starch in the bag 40 using a water flow pump with a filter. In addition, a substance that can control the hardness, for example, a plastic of which hardness changes by controlling the temperature, an electrorheological granular material of which hardness changes by controlling a current, and a magnetic granular material of which hardness changes by controlling a magnetic force may be used.

Shape

In the first embodiment, only the hardness of the bag 40 is focused on, but the shape of the bag 40 may be presented to the user U. In order to present an arbitrary shape, it is necessary to shape the bag 40 by hand or with a mold before it is put into the shoe 70. However, for example, the shape can be changed in a programmable manner by adding an actuator mechanism. Regarding the actuator to be added, for example, a variable frame composed of a plurality of linear actuators and an actuator that injects air are considered. In presentation of such a shape, a control method such as a method of using muscles to prevent falling during walking, for example, making a shape with the heel raised so that it is possible to use muscles such that the center of gravity of the body is forward can be considered.

Temperature

For example, a method in which an electronic component such as a peltier element of which temperature can be changed in a programmable manner is put into the bag 40 is considered. It is considered that, when the sole is heated, the blood flow is improved, and the muscle activity increases. Therefore, a control method such as performing heating so that the iEMG increases during walking is considered.

Pressure

For example, a method in which the air pressure in the bag 40 is programmably adjusted by the vacuum pump 19, and thus an arbitrary pressure is applied to a body part in contact with the bag 40 is considered. Since the user U feels a harder sensation when a stronger pressure is applied, it is conceivable to perform control such that the iEMG decreases during walking and the pressure applied to the body increases.

When presentation is performed in this manner, it is possible for the user U to actually learn what kind of operation should be performed or how to use the muscle.

Unit of One Operation

In the first embodiment, the unit of one operation is one step from when the heel of one foot touches the ground until it touches the ground again. However, the unit of one operation may be smaller or larger. For example, one operation may be separated by time such as every 100 [ms]. That is, the "feature value of the myoelectric potential" may be a feature value of every 100 [ms] instead of a feature value of the myoelectric potential for each step.

How to Set Purpose

In the first embodiment, in the target iEMG input subroutine in Step S23, it is assumed that a certain specific value is input. That is, control is performed in a procedure of approaching the target iEMG (feature value of the target myoelectric potential) by repeatedly increasing or decreasing the current iEMG (feature value of the current myoelectric potential). In addition to the procedure of controlling for a certain purpose (for example, matching the shape of EMG of a comparison subject professional person with the shape of one's own EMG), only the direction in change is determined and control may be performed in the direction. For example, if it is desired to increase the amount of muscle activity of a certain muscle, by inputting "a value larger than the 'feature value of the current myoelectric potential'" instead of inputting the "feature value of the target myoelectric potential" as a "certain specific value", control by the procedure of continuing to present the property of increasing the amount of muscle activity is also conceivable.

In addition, target biometric information which is target biometric information to be realized by the user may be input by a person other than the user U, biometric information registered in an external database or the like in advance may be set as an input, and target biometric information may be selected and set from a plurality of pieces of biometric information.

Timing to Change Hardness

In the first embodiment, the hardness presented by the walking user U according to one step completed immediately before is determined and the hardness presented for the next step is changed. However, the timing to change the hardness can be any timing. That is, the property may be changed during the current step. For example, it is also conceivable that, when the heel of one foot touches the ground, the hardness is changed so that the amount of muscle activity increases, and thus immediately after the heel touches the ground, the amount of muscle activity when the entire sole is in contact with the ground increases. Hereinafter, this will be described in more detail in a second embodiment.

Second Embodiment

Figures 14, 15:
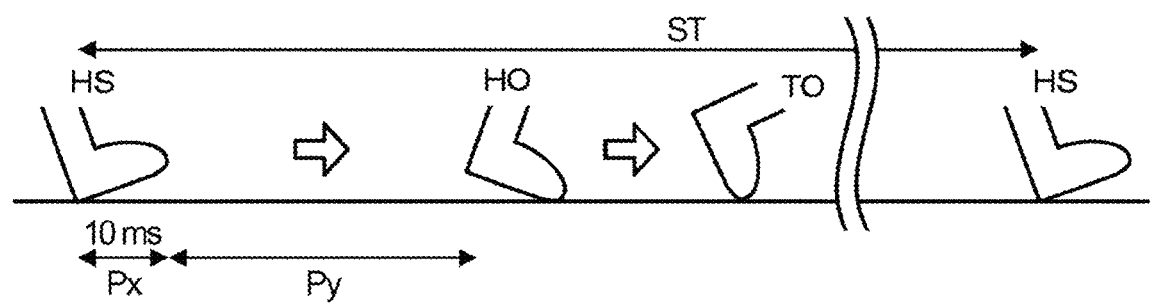
FIG. 14 is a schematic view for explaining a previous operation period Px and a main operation period Py in a living body guidance device according to a second embodiment.
FIG. 15 is a diagram showing a content example of a database unit provided in a storage of a user terminal.

FIG. 14 is a schematic view for explaining a previous operation period Px and a main operation period Py in a living body guidance device according to the second embodiment. In the second embodiment, in one step ST, a period when the state becomes a heel contact state HS in which the heel of the user U touches the ground is set as a previous operation X, and a period from the heel ground state HS to a heel takeoff state HO in which the heel is lifted is set as a main operation Y. Specifically, a period of 10 [ms] from when the pressure average value PA calculated from pressure measurement data from the pressure sensor 30 becomes the threshold value Th or more is regarded as a previous operation X, and a period from when 10 [ms] has elapsed after the pressure average value PA becomes the threshold value Th or more until it becomes less than the threshold value is regarded as a main operation Y.

In the living body guidance device according to the second embodiment, the living body guidance program stored in the storage 24 of the user terminal 20 and the content of the database unit 3 are different from those in the first embodiment. FIG. 15 is a diagram showing a content example of the database unit 3 provided in the storage 24. In the database unit 3, a plurality of estimated relationships, which are relationships between the value of the iEMG calculated in the previous operation period Px which is a period of the previous operation X and the value of the estimated iEMG in the main operation period Py which is a period of the main operation Y, can be recorded as an estimated relationship table in advance. In addition, in the database unit 3, the relationship between the hardness of the bag 40 and the iEMG of the main operation period Py is also registered. This may be similar to the hardness-iEMG table shown in FIG. 4.

Figure 16:
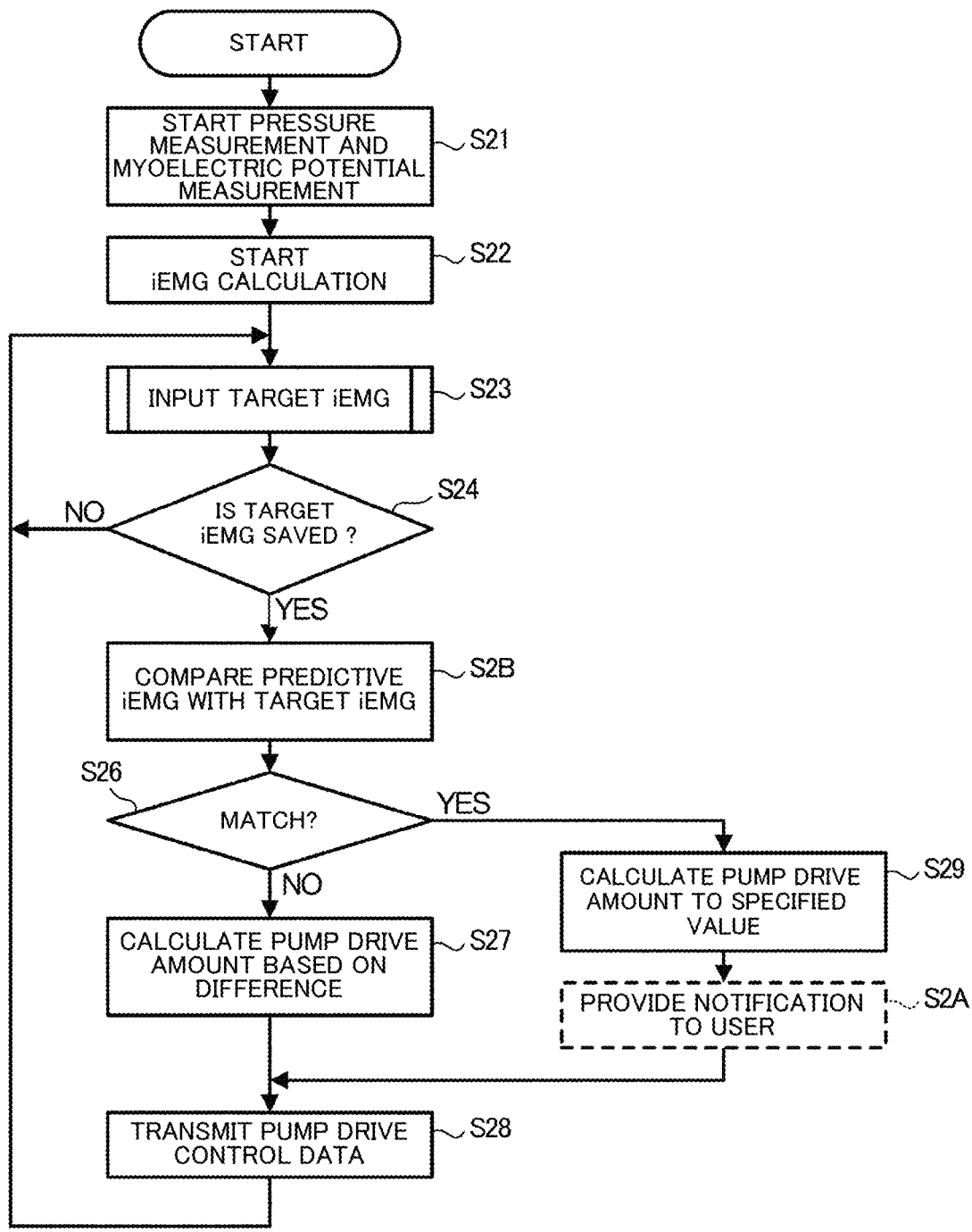
FIG. 16 is a main operation flowchart of a processor provided in a user terminal, which executes a living body guidance program according to the second embodiment.
Figure 17:
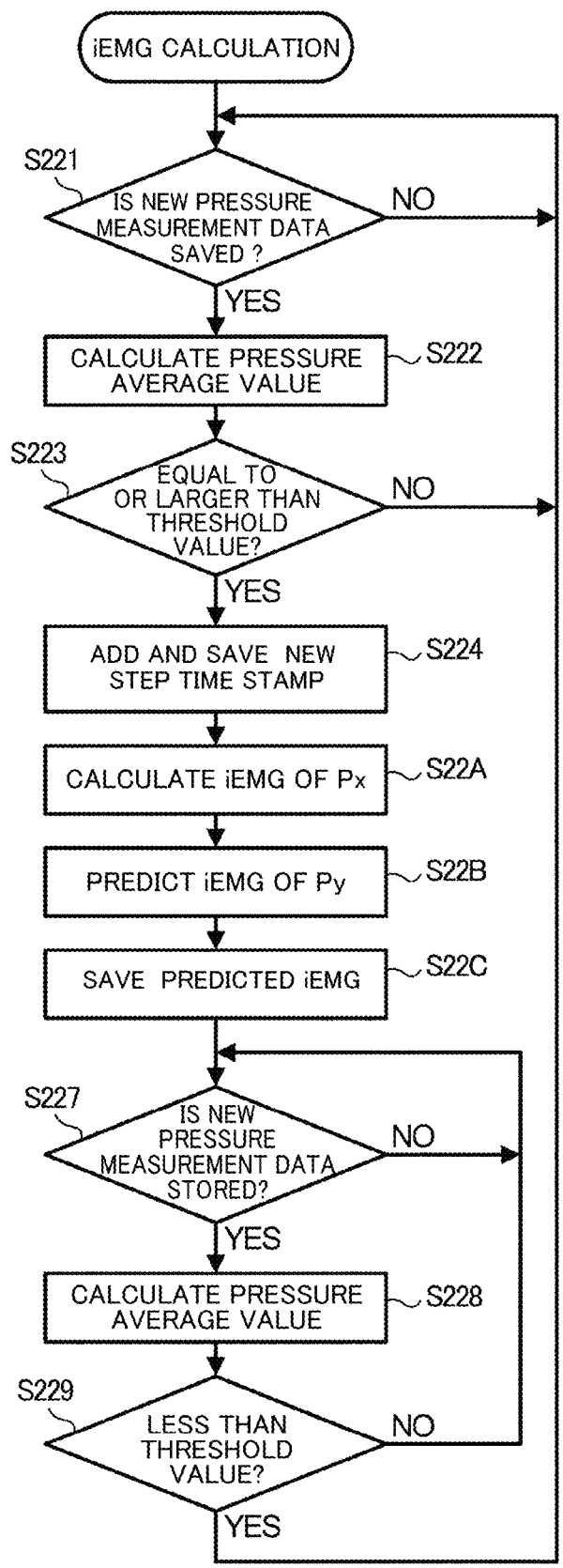
FIG. 17 is an operation flowchart of an IEMG calculation process performed by the processor.

FIG. 16 is a main operation flowchart of the processor 21 included in the user terminal 20, which executes the living body guidance program according to the second embodiment. FIG. 17 shows an operation flowchart of an IEMG calculation process performed by the processor 21. The living body guidance program according to the second embodiment causing the processor 21 to perform these operations is stored in the storage 24, and the operations shown in FIG. 16 and FIG. 17 can be performed when the processor 21 executes the living body guidance program. The same processes as in the first embodiment are denoted with the same reference numerals as those in FIG. 7 and FIG. 10.

As described in the first embodiment, when the processor 21 starts iEMG calculation in Step S22, the processor 21 calculates a pressure average value PA in Step S222 whenever it is determined that new pressure measurement data is saved in the RAM 23 in Step S221. Then, when the processor 21 determines in Step S223 that the calculated pressure average value PA is equal to or larger than the threshold value Th, in Step S224, a time at which the pressure average value PA changes from a value smaller than the threshold value Th to a value equal to or larger than the threshold value Th or more is regarded as a time at which the heel of the foot touches the ground, that is, a time at which the previous operation period Px starts, and the time is additionally saved in the RAM 23 as a new step start time stamp.

Then, in the second embodiment, the processor 21 calculates an iEMG for the previous operation period Px in Step S22A. This is a process in which all of the values of myoelectric potential measurement data saved in the RAM 23, which are measured within 10 [ms] from the time indicated by the start time stamp of the previous operation period Px additionally saved in the RAM 23 are added, and the addition result is used as an iEMG of the previous operation period Px. In Step S22B, the processor 21 calculates a predicted value of the iEMG of the main operation period Py corresponding to the calculated iEMG of the previous operation period Px using the database unit 3 provided in the storage 24. As a specific example, for example, the iEMG of the previous operation period Px is 10 [μV]. As shown in FIG. 15, in the database unit 3, 60 [μV] is registered as an iEMG of the main operation period Py with respect to the iEMG10 [μV] of the previous operation period Px. Therefore, the processor 21 calculates 60 [μV] as a predicted value of the iEMG of the main operation period Py. In Step S22C, the processor 21 saves the calculated predicted value of the iEMG of the main operation period Py as a predictive iEMG in the RAM 23. Then, the processor 21 advances the process to Step S227, and performs the process as described in the first embodiment.

In this manner, the processor 21 calculates an iEMG of a previous operation period Px which is biometric information measured by the myoelectric sensor 50 in the previous operation period Px which is the first period. Based on the iEMG of the previous operation period Px and the estimated relationship recorded in the estimated relationship table of the database unit 3, the processor 21 can realize the function of the current state determining unit 5 that estimates the predictive iEMG which is current biometric information in the main operation period Py that is the second period following the first period.

In the main operation, when the processor 21 determines that the target iEMG is saved in Step S24, in the second embodiment, in Step S2B, the predictive iEMG saved in the RAM 23 and the set target iEMG are compared. Then, the processor 21 determines whether comparison results match in Step S26.

When it is determined that comparison results do not match, the processor 21 calculates a drive amount of the vacuum pump 19 based on the difference between them in Step S27. That is, the processor 21 searches the hardness-iEMG table in the database unit 3 for the hardness of the bag 40 that can realize an iEMG closer to the target iEMG, and calculates a drive amount of the vacuum pump 19 for making the bag 40 have the hardness based on the hardness-drive amount table.

For example, when the target iEMG is larger than the predictive iEMG, the processor 21 can search the hardness-iEMG table for the hardness that can realize an iEMG larger than the predictive iEMG. On the other hand, when the target iEMG is smaller than the predictive iEMG, the processor 21 can search the hardness-iEMG table for the hardness that can realize an iEMG smaller than the predictive iEMG.

As a specific example, for example, when the target iEMG is 70 [μV], and the predictive iEMG is 60 [μV], the target iEMG is larger than the predictive iEMG and the difference between them (target iEMG-predictive iEMG) is 10 [μV]. Here, when the content of the hardness-iEMG table is as shown in the example of FIG. 4, since the value of the iEMG corresponding to "hard" searched from the hardness-iEMG table is 30 [μV], the difference from the predictive iEMG (hard iEMG-predictive iEMG) is −30 [μV]. Since the value of the iEMG corresponding to "soft" searched from the hardness-iEMG table is 70 [μV], the difference from the predictive iEMG (soft iEMG-predictive iEMG) is 10 [μV]. Between these −30 [μV] and 10 [μV], since 10 [μV] is closer to the difference of 10 [μV] between the target iEMG and the predictive iEMG (small difference), "soft" is searched for as the hardness of the bag 40 that realizes it. The processor 21 calculates a drive amount of the vacuum pump 19 for the bag 40 to set in this "soft" state. The drive amount of the vacuum pump 19, for example, the drive amount of the vacuum pump 19 corresponding to the hardness "soft" of the bag 40 can be calculated from, for example, a relationship between the drive amount of the vacuum pump 19 and the hardness of the bag 40 separately determined and registered as a hardness-drive amount table in the database unit 3.

The drive amount of the vacuum pump 19 may be calculated by a method other than the above method. For example, when the target iEMG is 70 [μV] and the predictive iEMG is 60 [μV], the hardness-iEMG table in the database unit 3 is searched for an iEMG closer to the target iEMG, and thus the hardness of the bag 40 corresponding to the iEMG is obtained. In this case, the hardness of the bag 40 corresponding to the iEMG closer to the target iEMG is "soft" in which the iEMG is 70 [μV]. The processor 21 calculates a drive amount of the vacuum pump 19 corresponding to the hardness "soft" of the bag 40 from, for example, a relationship between the drive amount of the vacuum pump 19 and the hardness of the bag 40 separately determined and registered as a hardness-drive amount table in the database unit 3. In this case, when the degree of the hardness of the bag 40 in which the iEMG is the same as the target iEMG of 70 [μV] is not defined, based on the relationship between the iEMG, the hardness of the bag 40, and the drive amount of the vacuum pump 19, the drive amount of the vacuum pump 19 which is the target iEMG may be obtained by interpolating numerical values appropriately.

When it is determined that comparison results match in Step S26, the processor 21 calculates a drive amount of the vacuum pump 19 to the default value in Step S29.

Other processes are the same as those described in the first embodiment.

Figure 18:
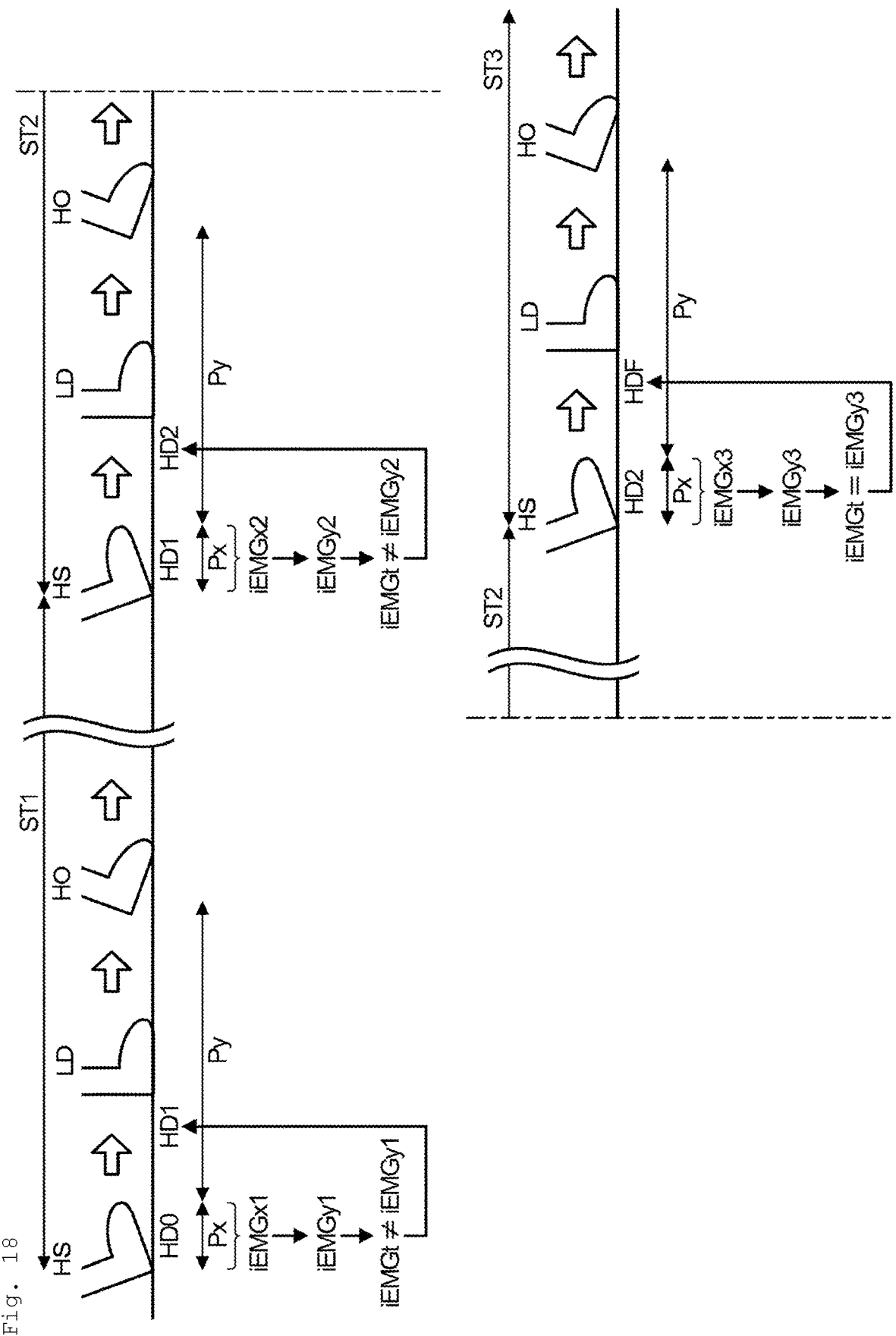
FIG. 18 is a schematic view for explaining operations of the living body guidance device.

FIG. 18 is a schematic view for explaining operations of the living body guidance device. In the second embodiment, in the previous operation period Px within 10 [ms] from when the state becomes the heel contact state HS in which the heel has touched the ground which is a walking start time of the first step ST1 of the user U, iEMGx1 which is an integral value of the myoelectric potential measured in this period is calculated. Then, based on the iEMGx1, an iEMGy1 which is a predictive iEMG for the main operation period Py after the previous operation period Px is completed is calculated, and the calculated iEMGy1 is compared with the iEMGt that is a target iEMG. When the iEMGy1 does not match the iEMGt, the hardness of the bag 40 is adjusted based on the difference between them. That is, the hardness HD0 which is the adjustment result one step before is changed to HD1 which is the hardness within the first step ST1. Depending on the hardness state of HD0, HD0=HD1 may be possible.

Similarly, iEMGx2, iEMGx3, are calculated at a walk start time of the second step ST2 of the user U, a walk start time of the third step ST3 of the user U, and based on calculated results, predicted values iEMGy2, iEMGy3, are calculated, and compared with iEMGt, and the hardness of the bag 40 in the second step ST2, the third step ST3, is adjusted according to the comparison results.

For example, when iEMGy3 and iEMGt match (iEMGt=iEMGy3) based on iEMGx3 calculated when walking of the third step ST3 starts, the processor 21 determines in Step S26 that comparison results of the predictive iEMG and the target iEMG match. In this case, the processor 21 calculates a drive amount of the vacuum pump 19 to the default value in Step S29. That is, the processor 21 calculates a drive amount of the vacuum pump 19 for making the hardness of the bag 40 be a prescribed hardness. In Step S28, the processor 21 transmits pump drive control data indicating the calculated drive amount of the vacuum pump 19 to the controller 10 via the communication device 27. Thereby, the CPU 11 of the controller 10 can PWM-control the vacuum pump 19 and set the bag 40 to HDF with a prescribed hardness.

In this manner, the hardness of the bag 40 in the current step depends on the situation of the user U when the one step starts. Therefore, it is preferable to inform the user U in advance that the main operation itself in which the default hardness is presented is the target movement. That is, in the second embodiment, if the user U recognizes that the movement of the main operation Y when the bag 40 reaches the default hardness=target movement, the user U says, "The bag has now reached the default hardness! Please, do the current movement!", and continues the movement of one step he or she just performed.

Here, in the second embodiment, as indicated by the dashed line in FIG. 16, as Step S2A, the user U is informed when the main operation Y in which the default hardness of the bag 40 is presented starts, which is the time at which the target movement is achieved, or when it is detected that the operation matches the target movement, and thus the user U may be explicitly informed regarding which operation is the target movement.

In the second embodiment described above, as in the first embodiment, it is possible to apply a target movement that the user wants to realize, for example, an appropriate and safe tactile stimulus for guiding the user U to perform muscle activity, to the user U.

Here, the present invention is not limited to the above embodiments, and can be variously modified in implementation steps without departing from the spirit and scope thereof. For example, in one operation, a plurality of previous operations X and main operations Y may be set for shorter periods. In addition, the embodiments may be appropriately combined and implemented as possible, and in this case, combined effects are obtained. In addition, the embodiments include inventions at various steps, and various inventions can be extracted according to appropriate combinations in a plurality of disclosed constitutional requirements.

REFERENCE SIGNS LIST

1 Measurement unit
2 Stimulus unit
3 Database unit
4 Input unit
5 Current state determining unit
6 Comparison unit
7 Control unit
10 Controller
11 CPU
12, 22 ROM
13, 23 RAM
14, 24 Storage
15, 27 Communication device
16 Input/output interface
17, 28 System bus
18, 29 Power source
19 Vacuum pump
20 User terminal
21 Processor
25 Input device
26 Output device
30 Pressure sensor
31 Wiring
40 Bag
41 Pipe
50 Myoelectric sensor
60 Supporter
70 Shoe
71 Intermediate bottom
72 Insole

The invention claimed is:

1. A living body guidance device, comprising:
a measurement unit that measures biometric information of a user;
a stimulus unit that is installed in contact with the user's body and presents a tactile stimulus to the user;
a database unit that has a relationship between the tactile stimulus presented by the stimulus unit and the biometric information according to the tactile stimulus of the stimulus unit recorded;
an input unit that sets target biometric information that is target biometric information that the user wants to realize; and
a control unit that, when there is a difference between current biometric information that is current biometric information of the user estimated based on the measurement result by the measurement unit and the target biometric information set by the input unit, controls the tactile stimulus presented by the stimulus unit, based on the relationship recorded in the database unit, such that the difference is reduced, so as to the user such that the current biometric information approaches the target biometric information.

2. The living body guidance device according to claim 1, wherein a control of the tactile stimulus of the stimulus unit by the control unit includes control of at least one of the shape and hardness of the stimulus unit.

3. The living body guidance device according to claim 1, wherein the stimulus unit and the control unit use jamming transition.

4. The living body guidance device according to claim 1, wherein the biometric information includes a myoelectric potential or a feature value of the myoelectric potential.

5. The living body guidance device according to claim 1, further comprising
a current state determining unit that estimates the current biometric information based on the measurement result by the measurement unit,
wherein the current state determining unit estimates the biometric information measured by the measurement unit in a first period as the current biometric information in a second period following the first period, and
the control unit controls the tactile stimulus presented by the stimulus unit, based on the relationship recorded in the database unit, such that the difference between the target biometric information and the current biometric information in the second period is reduced, so as to guide the user such that the current biometric information approaches the target biometric information.

6. The living body guidance device according to claim 1, further comprising
a current state determining unit that estimates the current biometric information based on the measurement result of the measurement unit,
wherein the database unit further has an estimated relationship which is the relationship between the biometric information and the current biometric information recorded,
the current state determining unit estimates the current biometric information in a second period following a first period based on the biometric information measured in the first period by the measurement unit and the estimated relationship recorded in the database unit, and
the control unit estimates a difference between the target biometric information and the current biometric information in the second period, controls the tactile stimulus presented by the stimulus unit such that the estimated difference is reduced, so as to guide the user such that the current biometric information approaches the target biometric information.

7. A living body guidance method, wherein
a computer is caused to:
measure biometric information of a user;
receive target biometric information that is target biometric information that is desired of the user to realize;
when there is a difference between current biometric information that is current biometric information of the user estimated based on the measurement result of the biometric information of the user and the target biometric information, control, based on a relationship recorded in a database unit in which the relationship between a tactile stimulus presented to the user by a stimulus unit installed in contact with the user's body and the biometric information according to the tactile stimulus of the stimulus unit is recorded, the tactile stimulus presented by the stimulus unit such that the difference is reduced, so as to guide the user such that the current biometric information approaches the target biometric information; and
repeat, at least measurement of the biometric information and guiding of the user until the difference between the target biometric information and the current biometric information disappears or until the current biometric information stops changing.

8. A non-transitory computer-readable medium having computer-executable instructions that, upon execution of the instructions by a processor of a computer, cause the computer to function as:
- a measurement unit that measures biometric information of a user;
- an input unit that sets target biometric information which is target biometric information desired of the user to realize; and
- a control unit that, when there is a difference between current biometric information that is current biometric information of the user estimated based on the measurement result of biometric information of the user and the target biometric information, controls a tactile stimulus presented by a stimulus unit such that the difference is reduced by referring to a database unit provided in the storage that has a relationship between the tactile stimulus presented to the user by the stimulus unit that is installed in contact with the user's body and the biometric information according to the tactile stimulus of the stimulus unit recorded, so as to guide the user such that the current biometric information approaches the target biometric information, based on the relationship recorded in the database unit.

9. The non-transitory computer-readable medium according to claim 8, wherein a control of the tactile stimulus of the stimulus unit by the control unit includes control of at least one of the shape and hardness of the stimulus unit.

10. The non-transitory computer-readable medium according to claim 8, wherein the stimulus unit and the control unit use jamming transition.

11. The non-transitory computer-readable medium according to claim 8, wherein the biometric information includes a myoelectric potential or a feature value of the myoelectric potential.

12. The non-transitory computer-readable medium according to claim 8, further comprising
- a current state determining unit that estimates the current biometric information based on the measurement result by the measurement unit,
- wherein the current state determining unit estimates the biometric information measured by the measurement unit in a first period as the current biometric information in a second period following the first period, and
- the control unit controls the tactile stimulus presented by the stimulus unit, based on the relationship recorded in the database unit, such that the difference between the target biometric information and the current biometric information in the second period is reduced, so as to guide the user such that the current biometric information approaches the target biometric information.

13. The non-transitory computer-readable medium according to claim 8, further comprising
- a current state determining unit that estimates the current biometric information based on the measurement result of the measurement unit,
- wherein the database unit further has an estimated relationship which is the relationship between the biometric information and the current biometric information recorded,
- the current state determining unit estimates the current biometric information in a second period following a first period based on the biometric information measured in the first period by the measurement unit and the estimated relationship recorded in the database unit, and
- the control unit estimates a difference between the target biometric information and the current biometric information in the second period, controls the tactile stimulus presented by the stimulus unit such that the estimated difference is reduced, so as to guide the user such that the current biometric information approaches the target biometric information.

* * * * *